(12) United States Patent
Kondo et al.

(10) Patent No.: US 6,953,435 B2
(45) Date of Patent: Oct. 11, 2005

(54) BIOLOGICAL DATA OBSERVATION APPARATUS

(75) Inventors: Shinji Kondo, Kariya (JP); Noriaki Sakakibara, Kariya (JP); Toru Takemoto, Toyota (JP); Toshihiro Honda, Toyota (JP)

(73) Assignee: Kabushiki Gaisha K -and- S, Aichi (JP)

(*) Notice: Subject to any disclaimer, the term of this patent is extended or adjusted under 35 U.S.C. 154(b) by 0 days.

(21) Appl. No.: 10/314,245

(22) Filed: Dec. 9, 2002

(65) Prior Publication Data

US 2003/0109791 A1 Jun. 12, 2003

(30) Foreign Application Priority Data

| Dec. 10, 2001 | (JP) | 2001-375925 |
| Dec. 11, 2001 | (JP) | 2001-377083 |
| Jan. 7, 2002 | (JP) | 2002-000856 |
| Apr. 16, 2002 | (JP) | 2002-113656 |
| Oct. 30, 2002 | (JP) | 2002-316337 |

(51) Int. Cl.[7] ............................................... A61B 5/02
(52) U.S. Cl. .................... 600/485; 600/301; 600/504
(58) Field of Search ............................... 600/485–507, 600/526

(56) References Cited

U.S. PATENT DOCUMENTS

| 3,651,318 A | * | 3/1972 | Czekajewski ............... 600/431 |
| 5,269,310 A | * | 12/1993 | Jones et al. ................. 600/480 |
| 5,289,823 A | * | 3/1994 | Eckerle ....................... 600/492 |
| 5,309,916 A | | 5/1994 | Hatschek |
| 5,485,848 A | * | 1/1996 | Jackson et al. ............. 600/485 |
| 5,776,071 A | * | 7/1998 | Inukai et al. ............... 600/493 |
| 6,354,999 B1 | * | 3/2002 | Dgany et al. ............... 600/486 |
| 6,356,775 B1 | * | 3/2002 | Kondo et al. ............... 600/346 |

FOREIGN PATENT DOCUMENTS

| EP | 0804899 A1 | 11/1997 |
| EP | 1046373 A1 | 10/2000 |
| JP | 1-207035 | 8/1989 |
| JP | 6-189917 | 7/1994 |
| JP | 7-241288 | 9/1995 |
| JP | 9-294727 | 11/1997 |
| JP | 9-294728 | 11/1997 |
| JP | 10-184 | 1/1998 |
| JP | 10-262958 | 10/1998 |
| JP | 11-76233 | 3/1999 |
| JP | 2000-83911 | 3/2000 |
| JP | 2001-000399 | 1/2001 |
| JP | 2001-99463 | 4/2001 |
| JP | 2001-149326 | 6/2001 |
| JP | 2001-161650 | 6/2001 |
| WO | 00/55579 | 9/2000 |

* cited by examiner

Primary Examiner—Robert L. Nasser
Assistant Examiner—Patricia Mallari
(74) Attorney, Agent, or Firm—Wenderoth, Lind & Ponack, L.L.P.

(57) ABSTRACT

A biological data observation apparatus includes a measuring unit including at least a photoelectric sensor including a light emitting element for emitting light with a predetermined wavelength onto a blood vessel of a subject and a light detecting element for detecting, as a photoelectric volume pulse wave, a change in an amount of transmitted or reflected light resulting from the light emitted from the light emitting section, a storage area in which pressure conversion data correlating a pulse wave area and a blood pressure value in order that the pulse wave area may be converted to the blood pressure value as an absolute value, the pulse wave area being obtained by integrating a wave form of the photoelectric capacity pulse wave per heartbeat, an operational unit calculating the pulse wave area on the basis of the photoelectric volume pulse wave obtained from the subject and further calculating the blood pressure value of the subject on the basis of the calculated pulse wave area and the blood pressure conversion data, and a display unit displaying a result of calculation performed by the operational unit.

14 Claims, 24 Drawing Sheets

LIGHT DETECTING ELEMENT 98C

LIGHT DETECTING ELEMENT 98B

PULSATION ANESTHETIC DEPTH $T_1 = (y_{1t} \cdot y_{5t} - k_1 \cdot y_{10} \cdot y_{50})/(k_2 \cdot y_{10} \cdot y_{50})$
WHERE $k_1$ AND $k_2$ ARE CONSTANTS.

PULSATION ANESTHETIC DEPTH $T_1 = (y_{1t} \cdot y_{5t} - k_1 \cdot y_{10} \cdot y_{50}) / (k_2 \cdot y_{10} \cdot y_{50})$
WHERE $k_1$ AND $k_2$ ARE CONSTANTS.

BIOLOGICAL DATA OBSERVATION APPARATUS

INCORPORATION BY REFERENCE

This application is based on Japanese Patent Application No. 2001-375925 filed on Dec. 10, 2001, No. 2001-377083 filed on Dec. 11, 2001, No. 2002-000856 filed on Jan. 07, 2002, No. 2002-113656 filed on Apr. 16, 2002, and No. 2002-316337 filed on Oct. 30, 2002, the content of which is incorporated hereinto by reference.

BACKGROUND OF THE INVENTION

1. Field of the Invention

This invention relates to a biological data measuring apparatus which measures biological data such as blood pressure, pulses, etc.

2. Description of the Related Art

In one conventional method of continuously measuring blood pressure values, a cuff is used to measure a blood pressure value of a subject at an initial stage of measurement and thereafter, a blood pressure value is calculated on the basis of transition of a photoelectric volume pulse wave obtained from a photoelectric sensor. Thus, both the cuff and the photoelectric sensor are commonly used at the initial stage of the measurement. Calibration is carried out to correlate each one of a photoelectric pulse wave (relative value) and a pressure pulsewave (absolute value) with the other. Once the calibration is carried out, a blood pressure value of the subject can subsequently be calculated only from the measurement by the photoelectric sensor without measurement by the cuff.

However, several times of pressure application against an artery of the subject inflict pain on him or her when the measurement with the cuff is done over again.

SUMMARY OF THE INVENTION

Therefore, an object of the present invention is to provide a biological data observation apparatus which can calculate a blood pressure value without the preparatory measurement with the cuff.

The present invention provides a biological data observation apparatus comprising a measuring unit including at least a photoelectric sensor including a light emitting element for emitting light with a predetermined wavelength onto a blood vessel of a subject and a light detecting element for detecting, as a photoelectric capacity pulse wave, a change in an amount of transmitted or reflected light resulting from the light emitted from the light emitting element, a storage area in which blood pressure conversion data correlating a pulse wave area and a blood pressure value in order that a pulse wave area may be converted to a blood pressure value as an absolute value, the pulse wave area being obtained by integrating a waveform of the photoelectric volume pulse wave per heartbeat, an operational unit calculating the pulse wave area on the basis of the photoelectric volume pulse wave obtained from the subject and further calculating a blood pressure value of the subject on the basis of the calculated pulse wave area and the blood pressure conversion data, and a display unit displaying a result of calculation performed by the operational unit.

According to the above-described biological data observation apparatus, the storage area stores the blood pressure conversion data in which the pulse-wave area of the photoelectric volume pulse-wave and blood pressure value are correlated with each other. Accordingly, when a photo electric volume pulse wave of the subject is measured by the photoelectric sensor, a blood pressure value of the subject is obtained from the pulse wave area of the photoelectric volume pulse wave and the blood pressure conversion data. Consequently, the above-described apparatus can eliminate the measurement of pressure pulse wave by a cuff in the initial stage of measurement and resultant calibration, whereupon the measuring procedure can be simplified.

BRIEF DESCRIPTION OF THE DRAWINGS

Other objects, features and advantages of the present invention will become clear upon reviewing the following description of embodiments, made with reference to the accompanying drawings, in which.

DETAILED DESCRIPTION OF THE INVENTION

Figure 1:
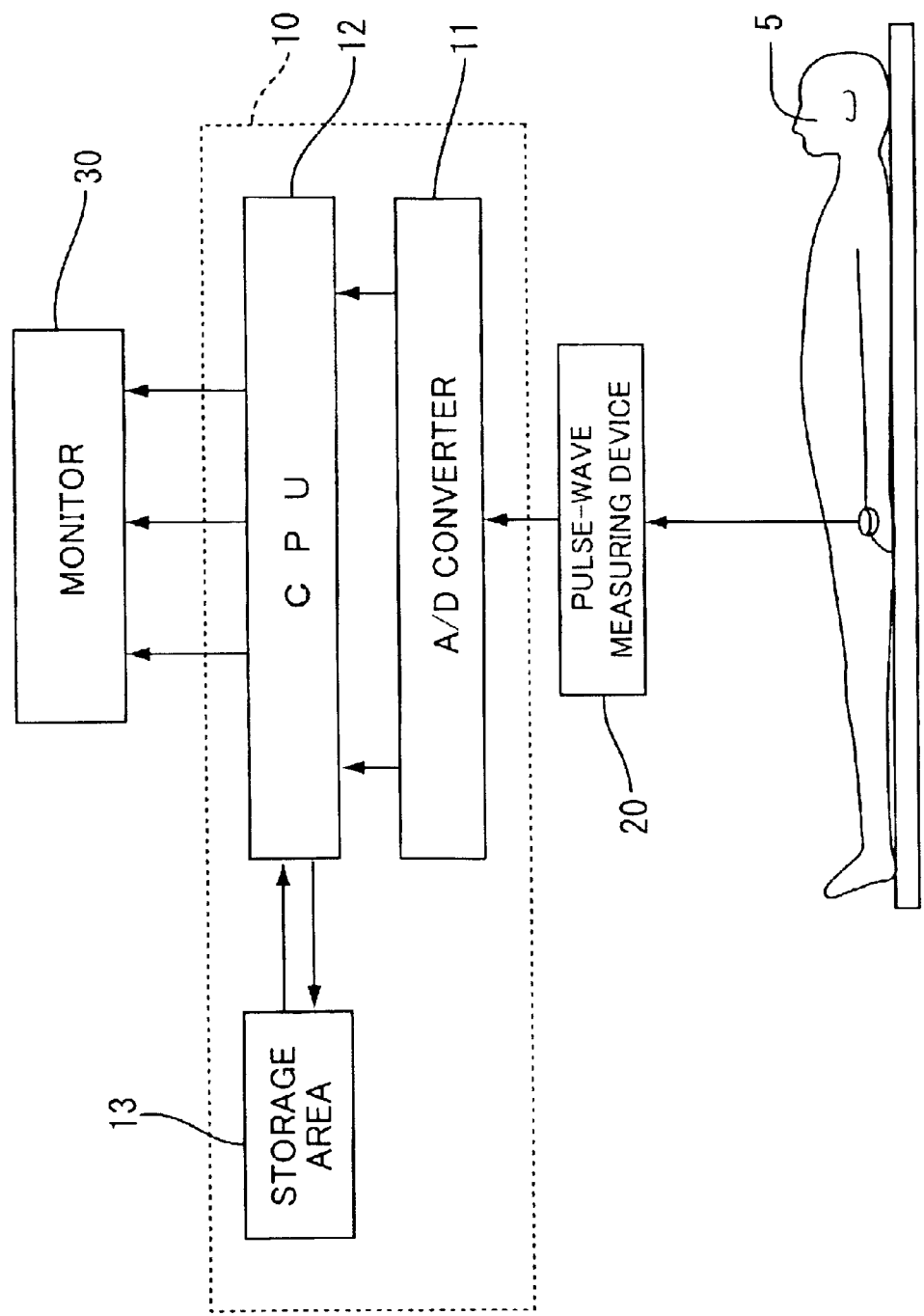
FIG. 1 is a block diagram of a biological data observation apparatus in accordance with a first embodiment of the present invention.

A first embodiment of the present invention will be described with reference to FIGS. 1 to 7. Referring to FIG. 1, a biological data observation apparatus in accordance with the first embodiment of the invention is shown. The biological data observation apparatus comprises a pulse-wave measuring device 20, a data processing device 10 connected to an output line of the pulse-wave measuring device 20 to carry out operational processing, and a monitor 30 (serving as a display unit in the invention) displaying results of operational processing by the data processing device 10. The pulse-wave measuring device 20 includes a photoelectric sensor 6 (serving as a measuring unit in the invention) irradiating light with a predetermined wavelength onto a blood vessel of a subject 5 thereby to detect, as a photoelectric volume pulse wave, a change in amount of resultant transmitted or reflected light.

The data processing device 10 includes an A/D converter 11, a CPU 12 (serving as an operational unit in the invention) and a storage area 13. The photoelectric volume pulse wave detected by the pulse wave measuring device 20 is continuously supplied via an A/D converter 11 into the CPU 12. The CPU 12 carries out operational processing on the basis of the digitized photoelectric volume pulse wave data, blood pressure conversion data written in the storage area 13, flow velocity conversion data, etc., thereby calculating a blood pressure value of the subject per heartbeat. The monitor 30 displays a blood pressure waveform and photoelectric volume pulse wave each in the unit of heartbeat.

Figure 2:
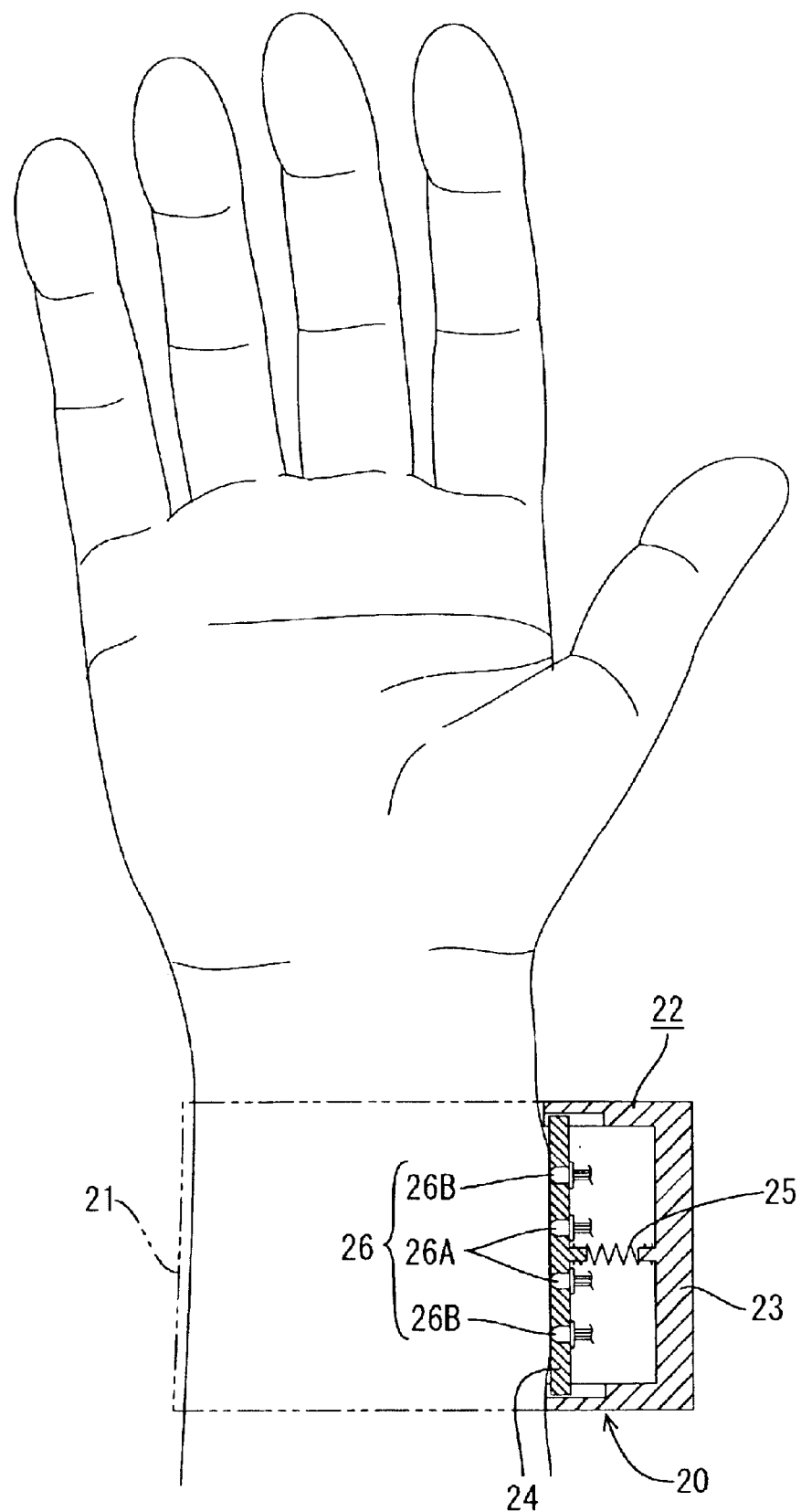
FIG. 2 is a sectional view of a pulse-wave measuring device.

Referring to FIG. 2, the pulse-wave measuring device 20 comprises a wrist band 21 and a body 22. The wrist band 21 has both ends adapted to be joined with each other so that the pulse-wave measuring device 20 is fixed around a wrist of the subject 5. The body 22 includes a casing 23 having an open side applied onto an arm of the subject 5 and a plate 24 closing the open side. The plate 24 is elastically supported by a coil spring 25 disposed between the casing 23 and the plate, so that the plate is usually pressed against a skin of the subject 5.

The plate 24 has a plurality of through holes into which a plurality of light emitting elements 26A and light detecting elements 26B are inserted from inside the casing 23 to be fixed. The light emitting elements 26A and light detecting elements 26B constitute a photoelectric sensor 26 for detecting a relative change in blood flow of the subject 5 as a change in an amount of light. Each light emitting element comprises a light-emitting diode (LED), whereas each light detecting element comprises a phototransistor. Each LED obtains output according to an amount of blood flow from the phototransistor. For example, light used for this purpose belongs to a wavelength range allowing light to be absorbed into and reflected on both oxyhemoglobin and deoxyhemoglobin in blood or light having a wavelength of about 640 mm is used. In this case, since output of the phototransistor changes with a change in the content of hemoglobin in blood, output obtained corresponds to a relative change in an amount of blood flow. The pulse-wave measuring device 20 includes a drive circuit (not shown) for driving the light emitting elements 26A and a receiving circuit (not shown) for processing an output signal delivered from the light detecting element 26B. Data of an obtained photoelectric volume pulsewave is transmitted via an output line to the data processing device 10.

A blood pressure value Pt of the subject is calculated mainly by operational processing in the embodiment as will be described later. The operational processing requires reference data of a blood pressure value Po and a flow velocity value Vo. For this purpose, the storage area 13 stores blood pressure conversion data for calculation of the blood pressure value Po and flow velocity conversion data for calculation of the flow velocity value Vo. Both data are obtained from experiments using a measuring artificial human body model 40 as will be described in detail later.

The measuring artificial human body model 40 reproduces a rested state of a sampling object with a standard form. The model 40 comprises a tank 41 storing an equivalent 49 to human blood (hereinafter, "blood equivalent"), a tube 42 through which the blood equivalent 49 is re-circulated and transferred, and a pump 43 pressure-feeding the blood equivalent 49 for every standard heartbeat time which is one of the sample person at rest, for example, 0.75 sec. The blood equivalent preferably has a similar composition as the human blood, and blood of any animal may be used, for example. The tube 42 serves as a pipe in the invention and corresponds to a blood vessel. The pressure of the pump 43 is adjustable. A flow rate sensor 44 is provided in the middle of the tube 42 for measuring a flow rate of the blood equivalent 49 per standard heartbeat time. The flow rate sensor 44 serves as a flow rate measuring section in the invention. A photoelectric sensor 45 is provided for detecting, as a change in an amount of light, a change in the flow rate of the blood equivalent 49 in the tube. A pressure measuring section 46 includes a container 47 partitioned by a rubber pressure valve 47A into upper and lower chambers and a pressure sensor 48 connected to the lower chamber side of the container 47. The tube 42 is connected to the upper chamber so that the blood equivalent can be re-circulated therein.

The tube 42 has an inner diameter approximately equal to one of a blood vessel in a wrist of the sample person in the rested state. The inner diameter of the tube 42 is set at 2.5 mm in the embodiment. The foregoing "rested state" is set because the artificial model 40 reproduces the rested state of the sample person. The blood vessel in the wrist is selected because a part of the subject where measurement actually is carried out is a wrist. It is desirable that the photoelectric sensor 26 of the pulse-wave measuring device 20 and the photoelectric sensor 45 of the artificial model 40 should be of the same type.

The pressure valve 47A is displaced downward upon pressure feed of the blood equivalent 49, whereby the pressure at the lower chamber side is varied to be rendered maximum. The pressure corresponding to a systolic blood pressure of the human body at rest is measured by the pressure sensor 48. On the other hand, the pressure valve 47A is moved to the upper chamber side after pressure feed of the blood equivalent 49, whereby the pressure at the lower chamber side is varied to be rendered minimum. The pressure corresponding to a diastolic blood pressure of the human body at rest is measured by the pressure sensor 48.

Further, output lines of the photoelectric sensor 45, flow-rate sensor 44, pressure sensor 48 are connected to the A/D converter 11. In the artificial model 40 constructed as described above, the pressure at which the blood equivalent 49 is pressure-fed by the pump 43 is changed to various values so that the photoelectric volume pulse wave and the pressure value of the blood equivalent 49 are measured by the photoelectric sensor 45 and the pressure sensor 48 every time of setting respectively, whereupon the subsequent blood pressure conversion data and flow rate conversion data are calculated. See FIGS. 4A to 4C.

In the blood pressure conversion data, a pulse wave area obtained by integrating the photoelectric volume pulse wave regarding the tube 42 per heartbeat and the blood pressure value of the blood equivalent obtained from the pressure sensor 48 are correlated with each other. The blood pressure conversion data is calculated at every systolic blood pressure and every diastolic blood pressure. See FIG. 4C. On the other hand, the pulse wave area and flow velocity value are correlated with each other in the flow velocity conversion data. See FIG. 4B. The flow velocity value is obtained by dividing a flow rate measured by the flow rate sensor 44 by a sectional area of the tube 42.

Figure 5:
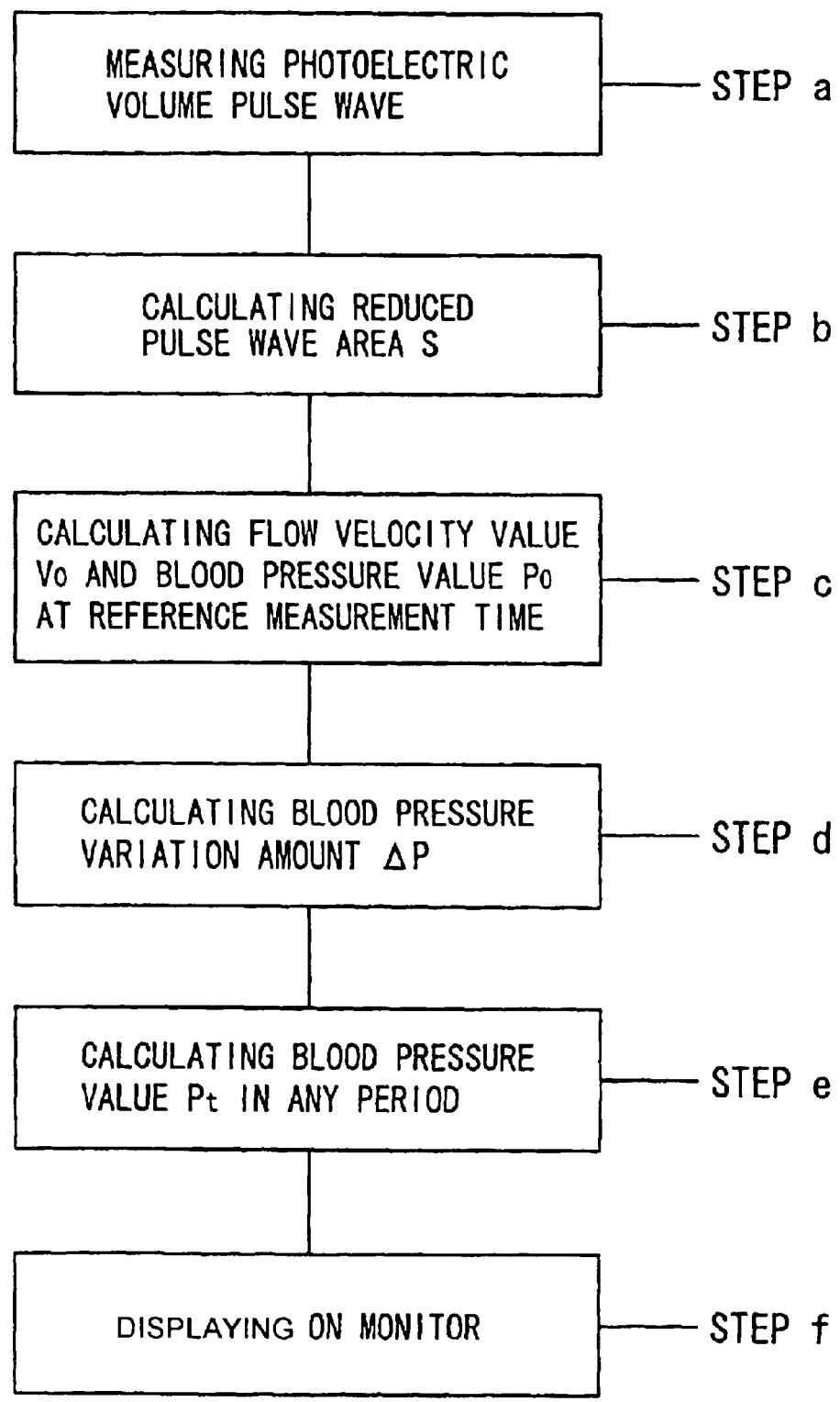
FIG. 5 is a flowchart showing a procedure for calculating a blood pressure value of a subject.
Figure 6:
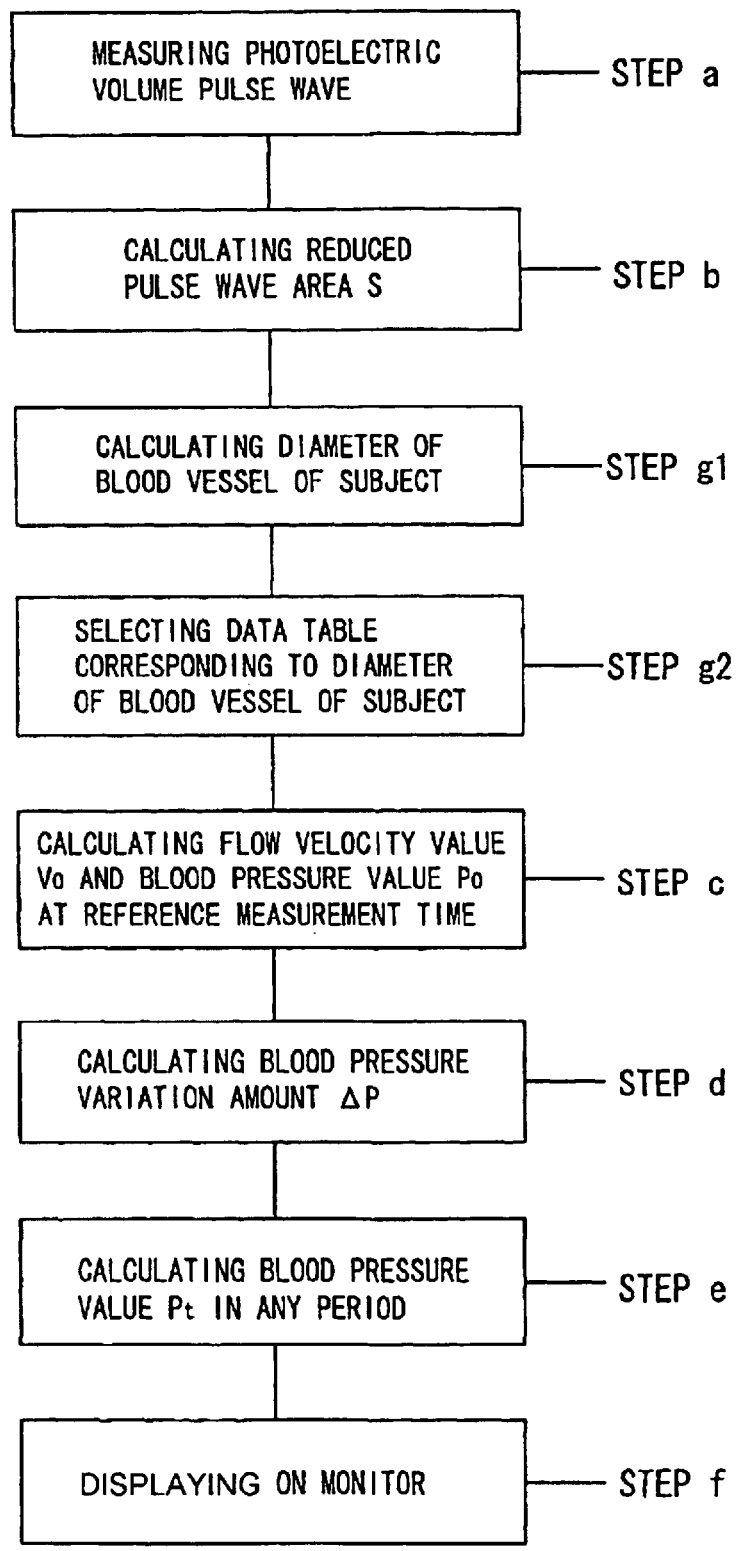
FIG. 6 is a flowchart showing another procedure for calculating a blood pressure value of a subject.
Figure 7:
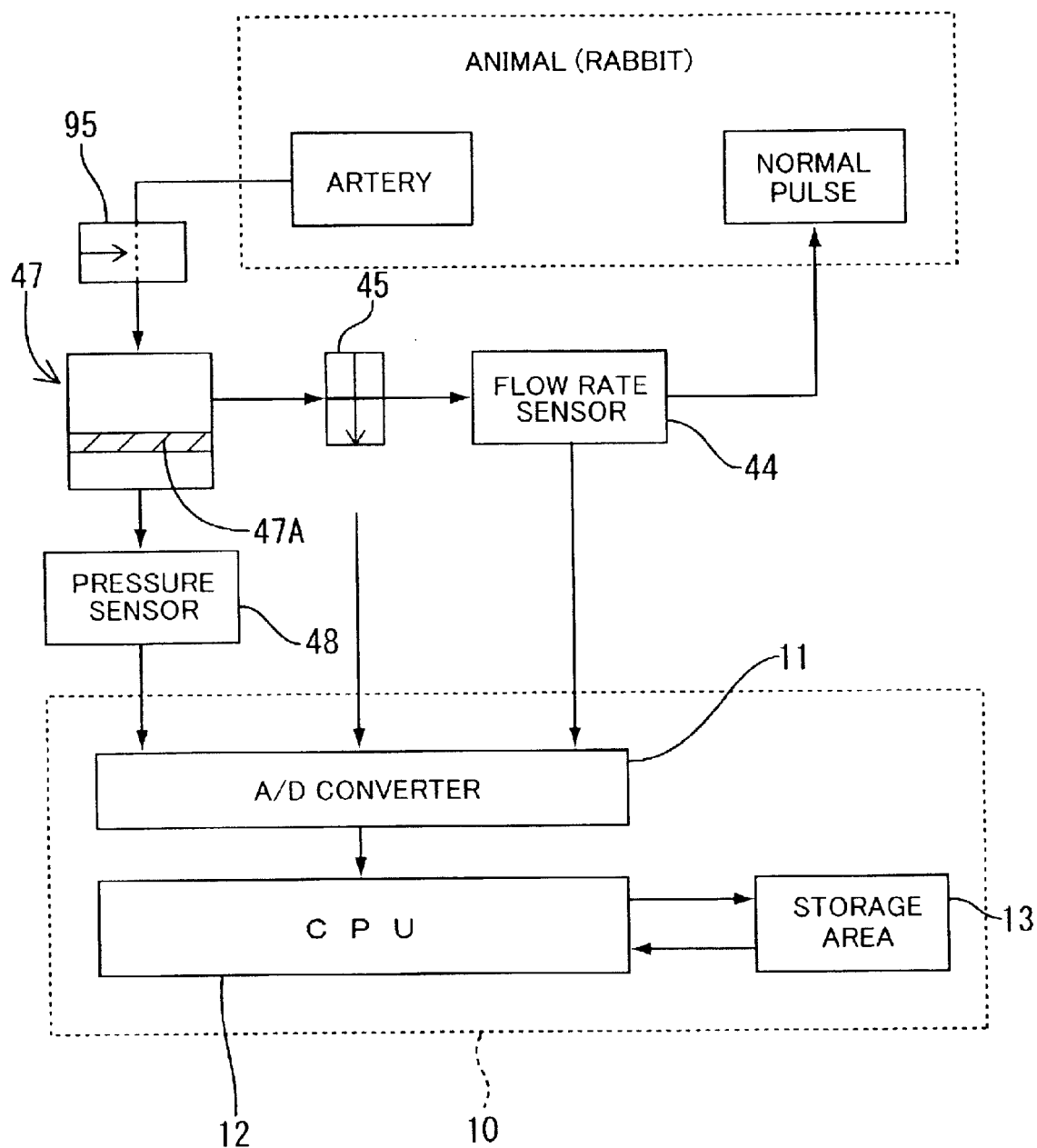
FIG. 7 is a block diagram of a measuring artificial human body model including an animal constituting an artificial human body part.

A manner of calculating a blood pressure value Pt in any period will be described with reference to FIG. 5. Firstly, a wrist band 21 is fastened around an arm of the subject 5, and the pulse-wave measuring device 20 is set so that the photoelectric sensor 26 is located above a blood vessel of the subject 5. When the photoelectric sensor 26 has been set, a photoelectric volume pulse wave is measured by the sensor 26 while the subject 5 is in a temporally rested state or measurement reference state (measurement reference time). The measured photoelectric volume pulse wave is delivered via the A/D converter 11 to CPU 12 (step a).

The subject 5 is rested under the above-noted condition. Accordingly, a mean value of the inner diameter of the subject's blood vessel takes approximately the same value as the inner diameter of the tube 42 although the inner diameter value of the subject's blood vessel varies to some extent. Consequently, reference blood pressure and flow velocity values Po and Vo can be calculated on the basis of the blood pressure data and flow velocity conversion data respectively. However, both data cannot be used when the subject changes from a rested state to a non-rested state such that the inner diameter of the blood vessel differs from the inner diameter of the tube 42 as the result of expansion and contraction of the blood vessel.

The procedure for calculation of the blood pressure value Po and flow velocity value Vo will be described more specifically. A pulse wave area per heartbeat is calculated on the basis of the photoelectric volume pulse wave (relative value) of the subject 5. The pulse wave area per heartbeat is converted to a value per above-mentioned standard heartbeat time (step b). For example, a pulse wave area s2 is converted to a value per standard heartbeat time t2 as follows:

$$s2 = s1 \cdot t2/t1$$

where t1 is a heartbeat time of the subject, t2 is a standard heartbeat time and s1 is a pulse wave area of the subject 5 per heartbeat. Reference symbol "S" will hereinafter designate the converted pulse wave area s2.

Figure 4A:
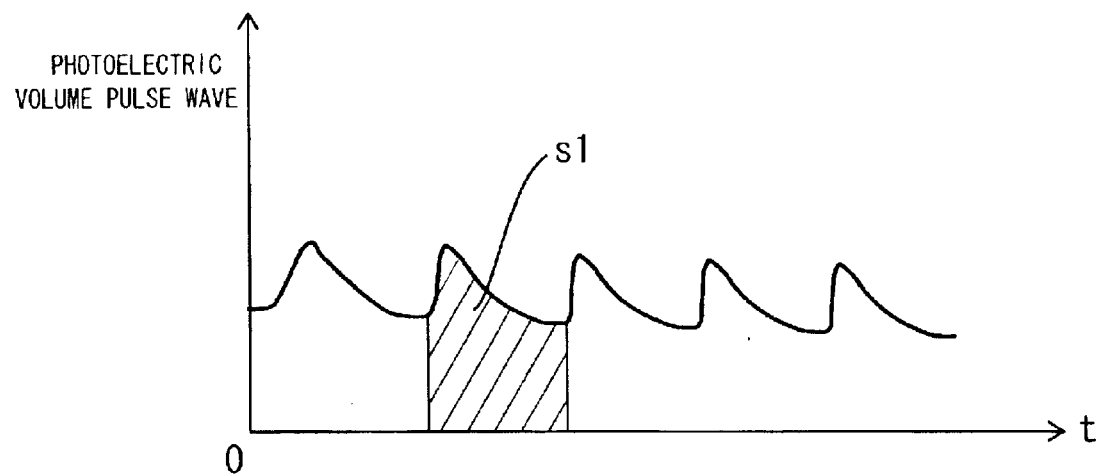
FIG. 4A is a waveform chart of photoelectric volume pulse-wave.
Figure 4B:
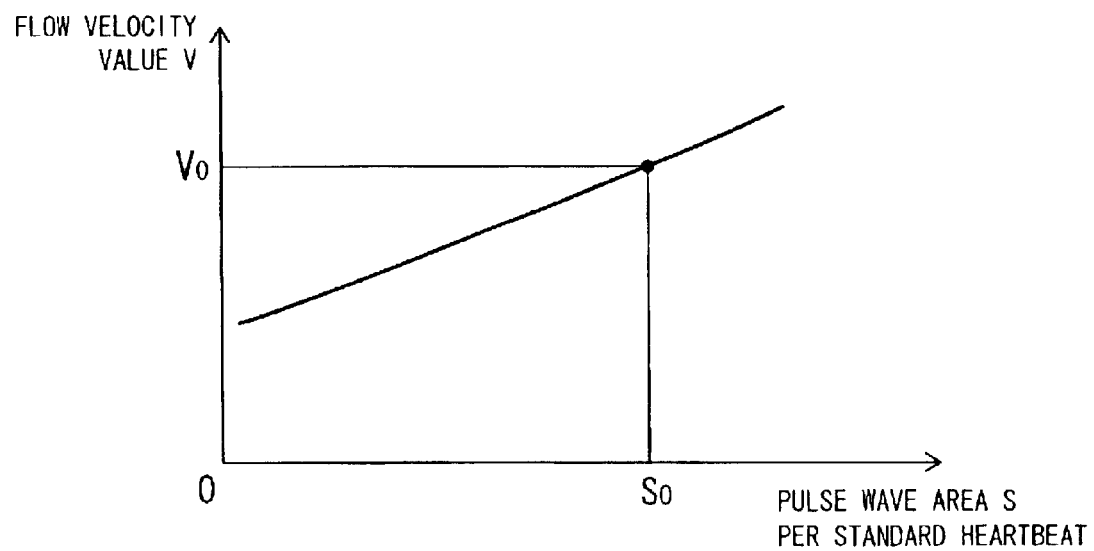
FIG. 4B is a graph showing a correlation between a pulse-wave area and a flow velocity value.
Figure 4C:
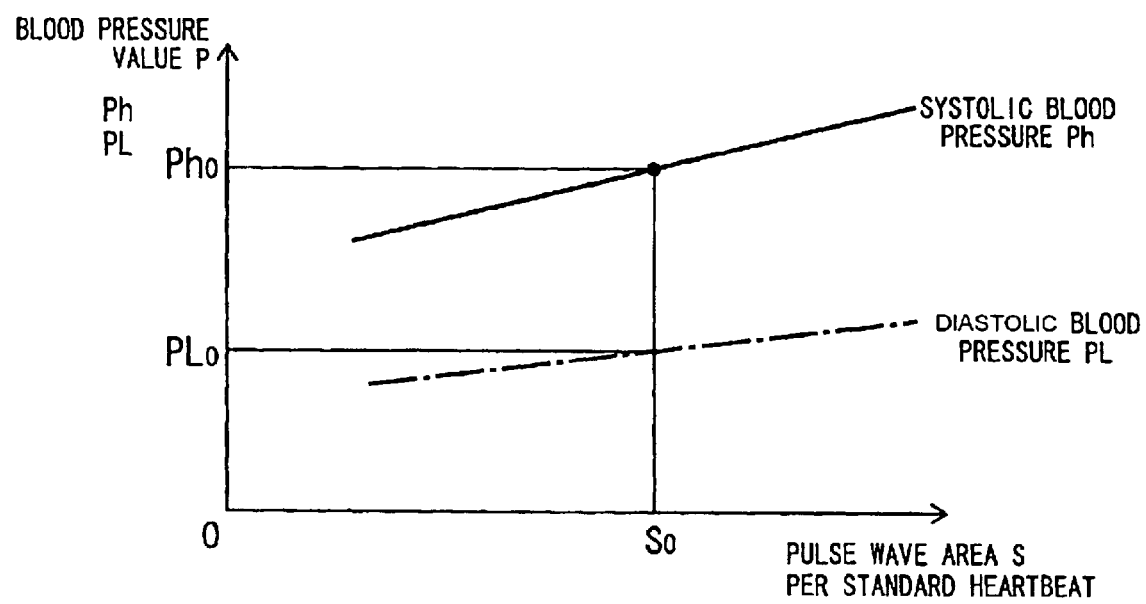
FIG. 4C is a graph showing a correlation between the pulse-wave area and a blood pressure value.

A flow velocity value (absolute value) in the measurement reference state is calculated from the converted pulse wave area S and flow velocity conversion data as shown in FIG. 4B (step c). For example, the flow velocity value is represented by Vo when the converted pulse wave area S is represented by So. Further, the blood pressure value (absolute value) of the subject 5 in the measurement reference state is calculated from the converted pulse wave area S and the blood pressure conversion data as shown in FIG. 4C (step c). When the converted pulse wave area is represented by So, the blood pressure value Po is represented as systolic blood pressure value Pho and diastolic blood pressure value PLo.

When the reference blood pressure value Po and flow velocity Vo are obtained in the above-described manner, the blood pressure value Pt is thereafter calculated by the following operational processing in a suitable period. The inventors have found that there is a correlation between an inner diameter of a blood vessel and a peak value of a photoelectric volume pulse wave. For example, the following relationship holds:

$$Do/Dt = k \cdot \phi o/\phi t \tag{1}$$

where Do is a peak value of the photoelectric volume pulse wave at the measurement reference time, φo is an inner diameter of blood vessel, Dt is a peak value of the photoelectric volume pulse wave in any period after the measurement reference time, and φt is an inner diameter of a blood vessel. Accordingly, the inner diameter φt of the subject's blood vessel can be calculated on the basis of the peak values Do and Dt of the photoelectric volume pulse wave. Further, since the product of a sectional area of a tube and a flow velocity of a liquid flowing through the tube is constant, the following relationship holds between a flow velocity value Vo of the blood at a measurement reference time and a flow velocity Vt of the blood in any period:

$$\pi(\phi o/2)^2 \cdot Vo = \pi(\phi t/2)^2 \times Vt \tag{2}$$

Accordingly, the following equation (3) is obtained on the basis of the equations (1) and (2) such that the flow velocity value Vt of the subject 5 in any period can be calculated:

$$Vt = (Do/kDt)^2 \cdot Vo \tag{3}$$

A blood pressure variation ΔP refers to a variation in the blood pressure value in any period relative to the value at a measurement reference time. The blood pressure variation ΔP is calculated on the basis of the calculated flow velocity value Vt in any period, the flow velocity value Vo at the measurement reference time and the blood pressure value Po at the measurement reference time (step d). More specifically, a relation expressed by the following equation (4) holds between the flow velocity and blood pressure values Vo and Po at the measurement reference time and the flow velocity and blood pressure values Vt and Pt in any period. Equation (5) is obtained from the equation (4) Reference symbol ρ designates a density of blood.

$$Po + \rho Vo^2/2 = Pt + \rho Vo^2/2 \tag{4}$$

$$\Delta P = Pt - Po = \rho/2(Vo^2 - Vt^2) \tag{5}$$

$$Pt = Po + \Delta P \tag{6}$$

Accordingly, the blood pressure variation amount ΔP can be calculated on the basis of equation (5). As a result, the systolic blood pressure value Pho in the measurement reference state is substituted for "Po" in equation (6) in order that a systolic blood pressure Pht per heartbeat in any period may be calculated. In order that a diastolic blood pressure PLt per heartbeat in any period may be calculated, the diastolic blood pressure value PLo in the measurement reference state is substituted for "Po" in equation (6)(step e).

As obvious from the foregoing, the storage area 13 stores the blood pressure conversion data and flow rate conversion data. When the subject is in the measurement reference state (rested state), the reference flow velocity and blood pressure values Vo and Po are calculated on both conversion data respectively. Further, in any period after calculation of the reference flow velocity and blood pressure values Vo and Po, the blood pressure variation amount ΔP, which is a variation in the blood pressure value in any period relative to the value at a measurement reference time, can be obtained by operation from the peak values Do and Dt of the photoelectric volume pulse wave and the flow velocity value Vo at the measurement reference time. The blood pressure value Pt in any period is calculated on the basis of the obtained blood pressure variation amount ΔP. Consequently, once the reference flow velocity and blood pressure values Vo and Po are calculated, the blood pressure value Pt can be obtained by operation whether the subject 5 is in a rested state or not. Thus, the blood pressure value Pt in any period can be calculated on the basis of only the measurement of the photoelectric volume pulse wave by the photoelectric sensor 26 without measurement of pressure pulse wave by the cuff etc. As a result, the blood pressure measuring procedure can be simplified.

The "non-rested state" refers to a case where physical conditions of the subject 5 change with course of measurement such that the inner diameter of blood vessel of the subject is contracted or expanded as compared with the rested state.

Figure 3:
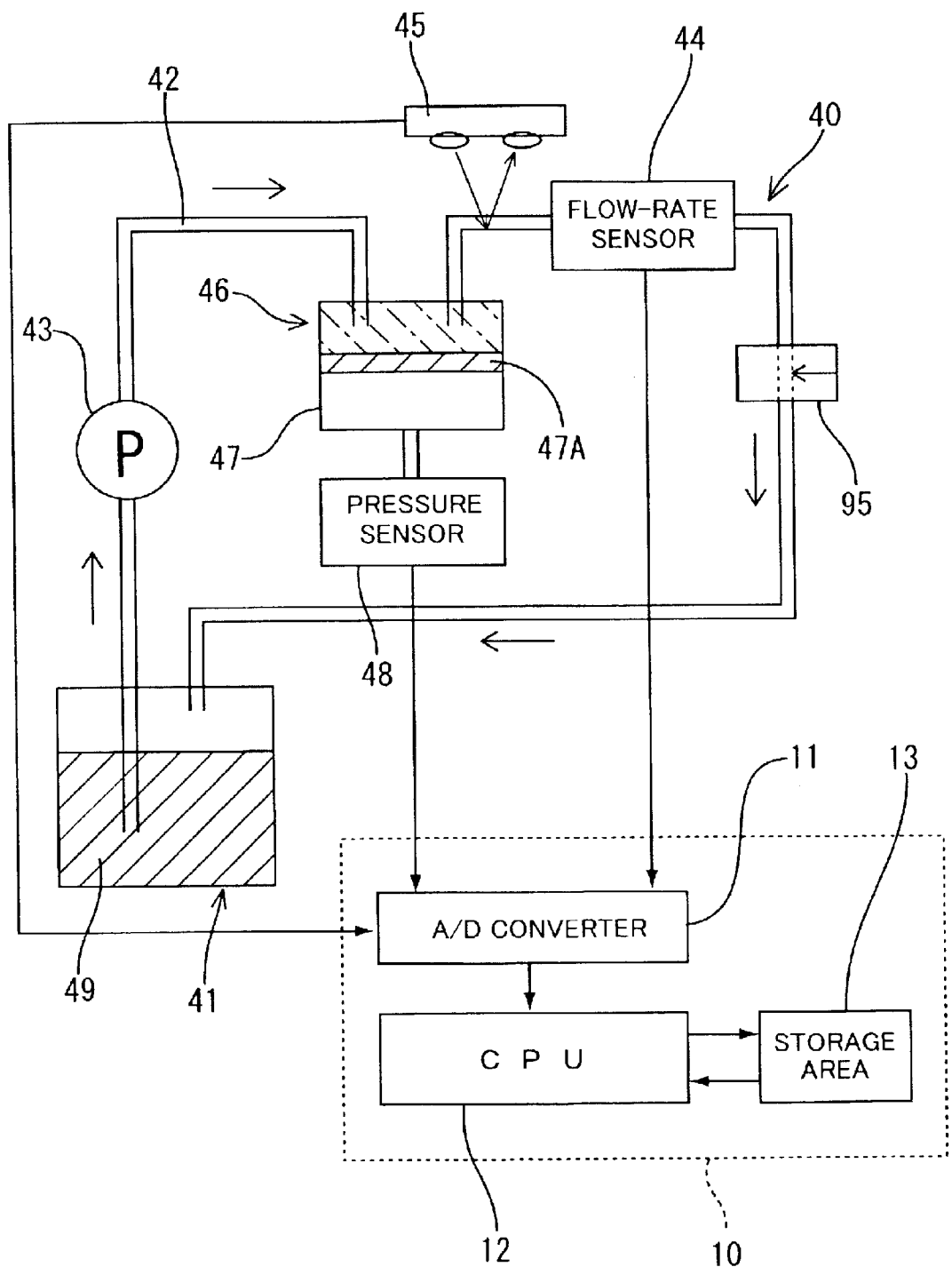
FIG. 3 is a block diagram of a measurement artificial human body model.

The artificial model 40 includes a laser displacement meter 95 built therein as shown in FIG. 3. The laser displacement meter 95 irradiates laser beams onto the tube 42. Light reflected on the tube 42 is condensed through a lens onto a light-receiving plane so as to be focused on it. The laser displacement meter 95 further measures an amount of displacement of a focal point on the light-receiving surface thereby to measure a variation in the inner diameter of the tube 42. More specifically, although the inner diameter of the tube 42 is 2.5 mm before the experiment, the tube 42 is expanded and contracted with variations in the pressure since the blood equivalent 49 is force-fed through the tube in the experiment. Accordingly, even when the inner diameter of the tube 42 is 2.5 mm in the natural state, there is a possibility that a mean value of the inner diameter of the tube under the experiment may not be 2.5 mm. In view of the problem, the inner diameter of the tube 42 is measured by the laser displacement meter 95 during the experiment, and a mean value of the inner diameter is obtained. When the obtained mean value is not 2.5 mm, the blood pressure and flow velocity conversion data measured using the tube 42 are amended or converted so that the data correspond to the inner diameter of 2.5 mm. As a result, an error in the inner diameter of the tube due to variations in the pressure applied to the tube 42 can be eliminated, whereupon an accurate blood pressure value can be obtained.

Further, the laser displacement meter 95 can be used to verify the blood pressure value obtained in any period (particularly in a non-rested state) from the equation (6). More specifically, the blood vessel is expanded or contracted in the non-rested state as compared with the rested state. For example, consider the case where a mean inner diameter value of the subject's blood vessel is 2.5 mm in the rested state. In this case, when the mean value changes from 2.5 mm to 4.0 mm with the subject's change from the rested state to the non-rested state, a tube 42 having the inner diameter of 2.5 mm is provided in the artificial model 40, and pressure is adjusted by a pump so that the mean value of the tube's inner diameter becomes 4.0 mm. A flow rate and pressure of the blood equivalent 49 are measured by the flow rate sensor 44 and the pressure sensor 48 respectively. The results of measurement are compared with the blood pressure value calculated on the basis of equation (6), whereby whether the blood pressure value is correct can experimentally be verified. Further, a correction factor or the like can be obtained when the blood pressure value calculated on the basis of equation (6) is compared with a blood pressure value actually measured in the experiment.

The blood pressure and flow velocity conversion data are based on data obtained when the tube has the inner diameter of 2.5 mm. However, in consideration of differences in the bodies of the subjects 5, blood pressure and flow velocity conversion data may be provided so as to correspond to different inner diameters of tubes. For example, the storage area 13 may store a plurality of data table, and tubes 42 for the respective sizes of 2.0 mm, 2.5 mm, 3.0 mm, etc. are prepared for the artificial model 40. Measurement is carried out with the tube 42 changed from one to another. The blood pressure data and flow velocity data are calculated for each tube 42 to be written onto the respective data table. Further, a blood vessel diameter measuring section serving as a measuring unit may be provided for measuring an inner diameter of blood vessel of the subject 5. In this case, a data table of tube diameter corresponding to the subject's blood vessel inner diameter is selected on the basis of the results of calculation. See steps g1 and g2 in FIG. 6. Consequently, the differences in the bodies of the subjects 5 can be eliminated and accordingly, a more accurate blood pressure value can be obtained.

As the above-mentioned blood vessel diameter measuring section, the photoelectric sensor 26 may be attached to a finger tip so that light with a predetermined wavelength is irradiated onto a regular pulse in the finger tip. The blood vessel diameter measuring section detects the resultant transmitted light. In this case, output to be obtained corresponds to the variations in the blood vessel diameter when the transmitted light belongs to a wavelength range in which the light is absorbed into a component in the blood vessel such as hemoglobin. Further, the inner diameter of the blood vessel can be measured on the basis of the variations in the flow velocity Vt. More specifically, the flow velocity value Vt varies with variations in the inner diameter of the blood vessel. The flow velocity is increased in a part of the blood vessel where the inner diameter thereof is reduced. The flow velocity is reduced in a part of the blood vessel where the inner diameter thereof is increased. Accordingly, when the flow velocity is measured at a plurality of parts of a single blood vessel, the inner diameter of the blood vessel can be obtained on the basis of the differences in the flow velocity Vt between the parts.

The above-described biological data observation apparatus can be used in the following manner. The photoelectric sensor 26 is disposed on different parts of a single blood vessel of the subject 5. A photoelectric volume pulse wave is measured at each part by the light emitting element 26A and the light detecting element 26B. A blood flow rate is then calculated for every measured part by the CPU 12. If the blood vessel is narrowed by arteriosclerosis, the flow rate of blood is reduced to a large degree at the narrowed part of the vessel. Accordingly, arteriosclerosis can be detected when the flow rates of blood calculated by the CPU 12 are compared with one another. In order that a flow rate of blood may be obtained by calculation, the flow velocity is initially calculated on the basis of the photoelectric volume pulse wave and flow velocity conversion data. The obtained flow velocity is multiplied by a sectional area of the blood vessel.

Further, the wrist band 21 of the pulse-wave measuring device 20 is modified so as to be fastened around the head and is set so that the photoelectric sensor 26 is directed to the skull. In this case, when light belonging to a predetermined wavelength range is irradiated from the light emitting element 26A of the photoelectric sensor 26, the irradiated light is transmitted through the skull so that the photoelectric volume pulse wave according to the blood flow rate in the blood vessel can be measured in a non invasive manner. Additionally, when the photoelectric sensor 26 is used to irradiate light onto another artery such as the radial artery or antebrachial artery, a photoelectric volume pulse wave can be measured according to a change in the blood flow rate in the artery.

The photoelectric sensor 26 constitutes the measuring unit in the foregoing embodiment. In a second embodiment, a second photoelectric sensor 96 is further provided in addition to the photoelectric sensor 26. Furthermore, the flow velocity values Vo and Vt of the subject 5 are calculated on the basis of the flow velocity conversion data in the foregoing embodiment. In the second embodiment, however, the second photoelectric sensor 96 detects a plurality of photoelectric volume pulse waves, and the flow velocity values Vo and Vt are calculated on the basis of a phase difference between the detected photoelectric volume pulse waves. The other arrangement in the second embodiment is similar to that in the foregoing embodiment and accordingly, detailed description of the other arrangement will be eliminated. The photoelectric sensor 26 serves as a first photoelectric sensor in the invention.

Figure 8:
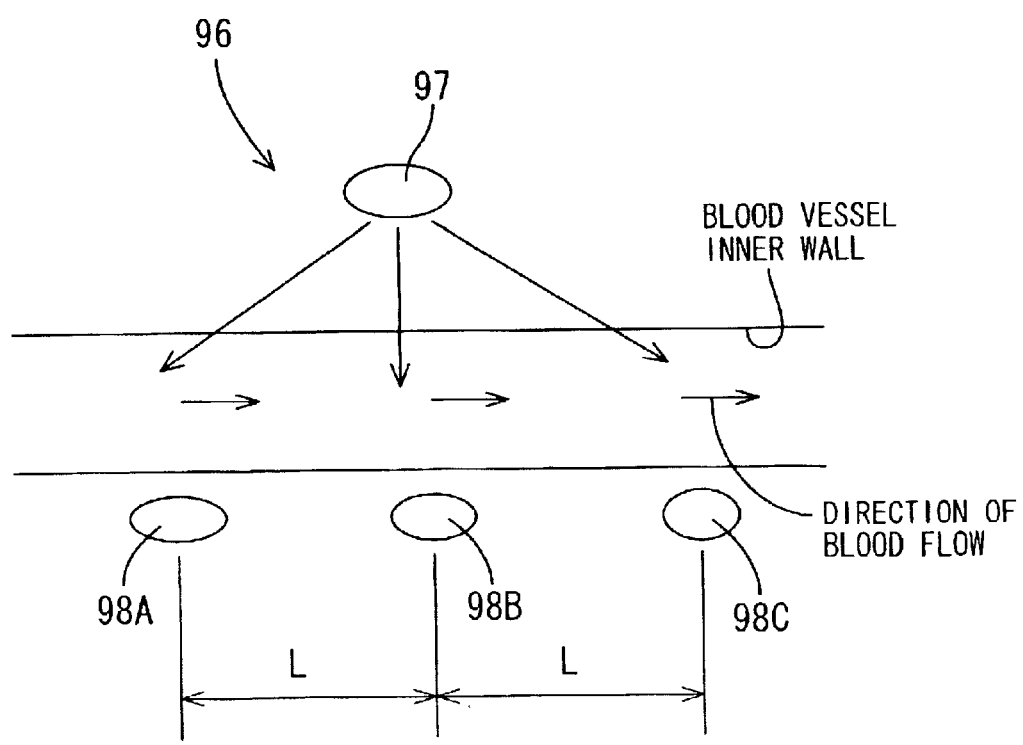
FIG. 8 illustrates a concept of another photoelectric sensor employed in the biological data observation apparatus in accordance with a second embodiment of the invention.
Figure 9A:
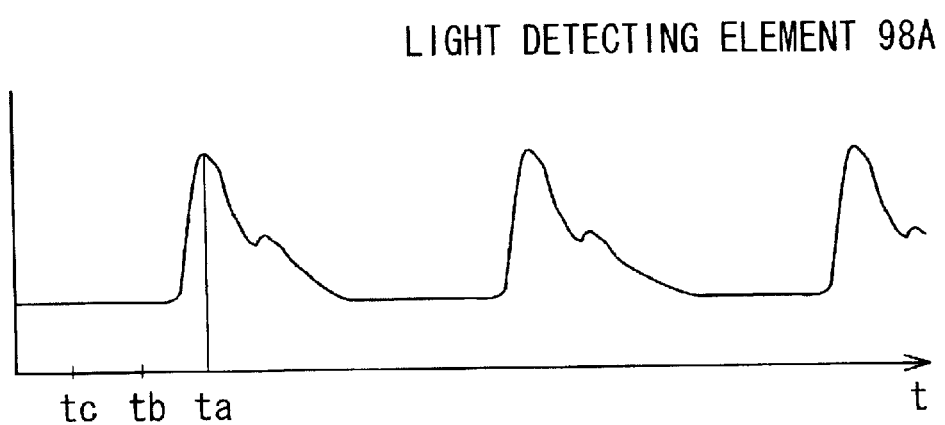
FIGS. 9A to 9C are graphs showing transition of the photoelectric volume pulse waves.
Figure 9C:
Figure 9B:
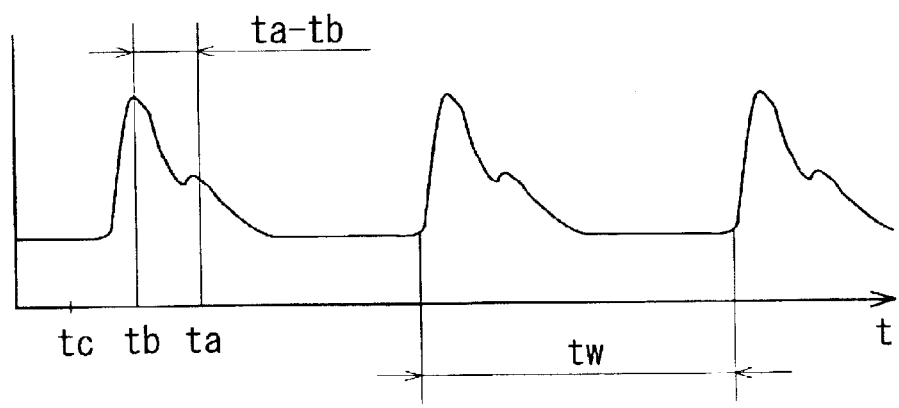
Figure 10:
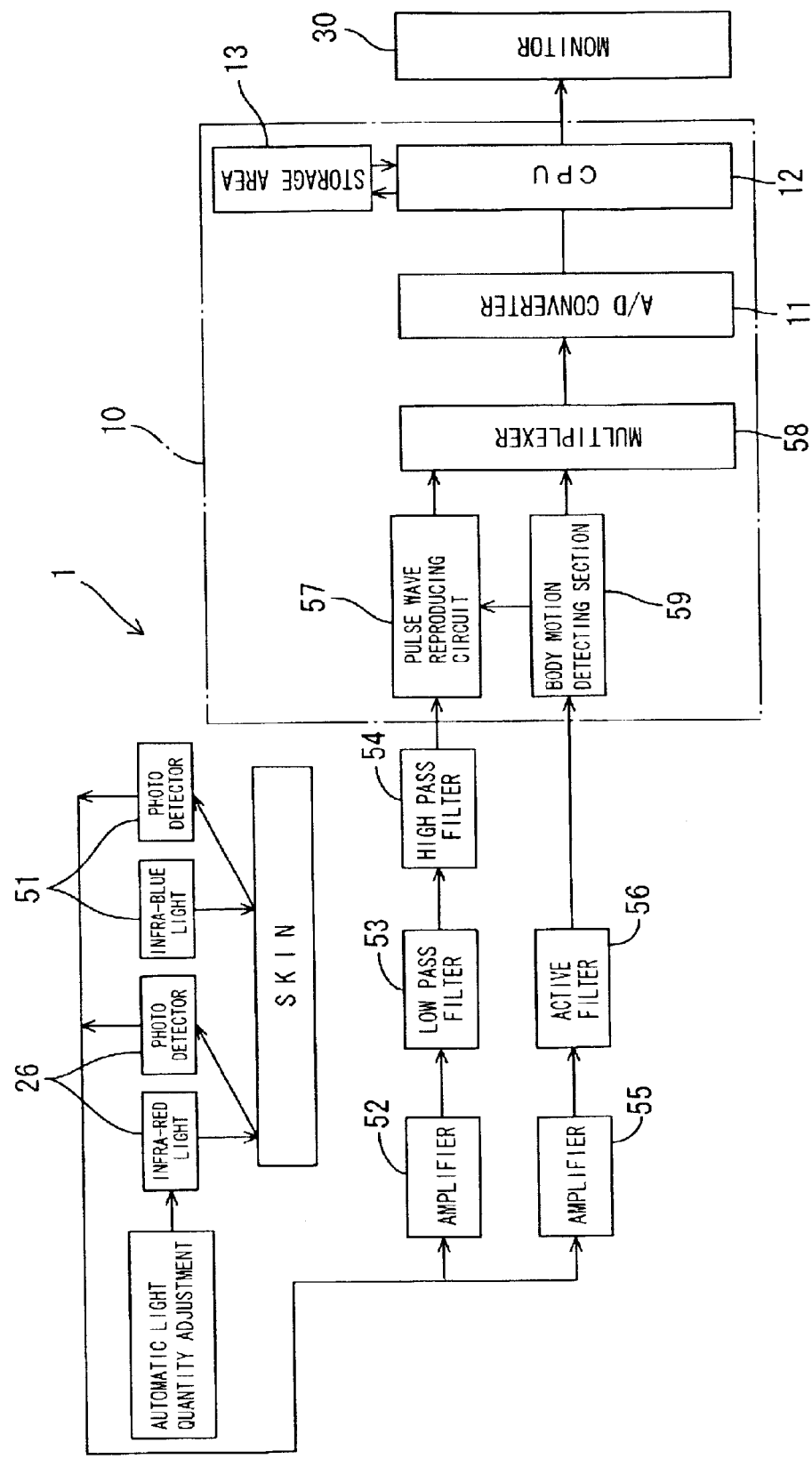
FIG. 10 is a block diagram of the biological data observation apparatus in accordance with a third embodiment of the invention.

The second photoelectric sensor 96 is applied around the wrist of the subject 5, for example, and comprises a single light emitting element 97 and a plurality of light detecting elements 98A, 98B and 98C. The light detecting elements 98A–98C are disposed at regular intervals L along the blood vessel and simultaneously detect light irradiated by the light emitting element 97 to be reflected (a transmitted light for convenience in explanation in FIG. 8). The interval L between the light detecting elements is set at a value ranging from several mm to several tens mm. Thus, when the interval between the light detecting elements is set at such a small value as mentioned above, a moving time required for the blood flow to move from the element 98A to the element 98C can be set at an equal value to a period of the photoelectric volume pulse wave. When the moving time of the blood flow is set in this manner, a moving time required for the blood flow to move between the light detecting elements can be obtained from a phase difference on graphs. FIGS. 9A to 9C illustrate transition of photoelectric volume pulse waves obtained from the light detecting elements 98A to 98C respectively. For example, reference symbols ta, tb and tc designate peak values of the photoelectric volume pulse waves respectively. A time required for the blood flow to move from the light detecting element 98A to the light detecting element 98B is expressed as "ta−tb" and the distance between the elements 98A and 98B is L. Accordingly, a flow velocity value Vt can be obtained from the following equation (7):

$$V=(ta-tb)/L \quad (7)$$

The values Vo and Vt can be obtained when the phase difference between the photoelectric volume pulse waves at the measurement reference time and in any period is substituted for (ta−tb) in equation (7). Additionally, three light detecting elements 98A to 98C are provided in the second embodiment. A flow velocity value between the elements 98A and 98B is obtained, and a flow velocity between the elements 98B and 98C is also obtained. A mean value of both flow velocity values serves as a flow velocity value in the second embodiment.

On the other hand, the blood pressure value Po at the measurement reference time can be obtained, as in the foregoing embodiment, on the basis of both converted pulse wave area So obtained from the photoelectric volume pulse wave and blood pressure conversion data. Accordingly, when the values Po, Vo and Vt are obtained, a blood pressure variation amount ΔP and accordingly, a blood pressure value Pt in any period can be obtained on the basis of equation (5):

$$\Delta P=Pt-Po=\rho/2(Vo^2-Vt^2) \quad (5)$$

Furthermore, the inventors have found that there is a correlation between the flow velocity value Vt and a period of the photoelectric volume pulse wave detected by each of the photoelectric sensors 26 and 96. Accordingly, when turning our attention to the period of the photoelectric volume pulse wave (for example, twin FIG. 9B), the transition of the flow velocity value can be obtained from the period of the photoelectric volume pulse wave without provision of a plurality of light detecting elements.

Both foregoing embodiments are directed to the measurement of blood pressure of the subject 5. However, a blood flow rate of the subject 5 can also be calculated on the basis of the blood pressure and flow velocity conversion data, for example. More specifically, a pressure sensor serving as the blood pressure measuring section in the invention) is provided as the measuring unit in stead of the photoelectric sensor 26. Firstly, a blood pressure value Po is obtained from the pressure sensor at the measurement reference time and furthermore, a converted pulse wave area and accordingly flow velocity values So and Vo are calculated on the basis of the blood pressure and flow velocity conversion data. Continuously, in any period after start of the measurement, the value Vt is calculated by substituting values for Pt, Po and Vo in equation (4) respectively. The value φt is further calculated by substituting values for φt, Vo and Vt. Consequently, a blood flow rate of the subject in any period can be obtained on the basis of the inner diameter of the blood vessel of the subject 5 and the flow velocity Vt of the blood.

A third embodiment of the invention will now be described with reference to FIGS. 10 to 12B. In the third embodiment, a body motion sensor 51 serving as the measuring unit is added for detecting a slight motion of the subject 5. Furthermore, a pulse wave reproducing circuit 57 and a body motion detecting section 59 are added to the data processing device 10. The body motion detecting section 59 constitutes part of the operational unit in the invention. A substituting process which will be described in detail later is carried out on the basis of determination of the waveform data of the photoelectric volume pulse wave and the results of determination. The other arrangement in the third embodiment is similar to that in the first embodiment and accordingly, detailed description of the other arrangement will be eliminated.

The body motion sensor 51 is disposed side by side with the photoelectric sensor 26 and comprises a blue LED (light emitting element) irradiating light with a wavelength of 420 mm, for example and a phototransistor (light detecting element) detecting the light reflected. The light emitted from the blue LED is reflected on a skin surface of the subject, and output of the phototransistor is detected as slight body movement of the subject 5.

The photoelectric sensor 26 is connected via an amplifier 52 to a low-pass filter 53 and a high-pass filter 54 so that output of the sensor 26 is supplied to the data processing device 10. The low-pass filter 53 cuts off frequencies at or below 30 Hz in order to eliminate low-frequency components as noise. Further, the high-pass filter 54 cuts off high-frequency components or frequencies at or above 150 Hz. The body motion sensor 51 is connected via an amplifier 55 to an active filter 56 (bandpass filter). The active filer 56 transmits a predetermined band of frequencies to the data processing device 10 while rejecting all other frequencies.

The data processing device 10 comprises a multiplexer 58, a pulse wave reproducing circuit 57 and a body motion detecting section 59 in addition to the storage area 13, CPU 12 and A/D converter 12. An input signal from the photoelectric sensor 26 is supplied via the pulse wave regenerating circuit 57 to the multiplexer 58 and CPU 12. An input signal from the body motion sensor 51 is supplied via the body motion detecting section 59 and multiplexer 58 to CPU 12.

The pulse wave reproducing circuit 57 is connected further to the body motion detecting section 59. In the pulse wave reproducing circuit 57, an output waveform of the body motion sensor 51 is subtracted from an output waveform delivered from the photoelectric sensor 26 to be passed through the filters 53 and 54. Thus, the pulse wave reproducing circuit 57 generates a waveform in which the body motion components (particularly slight body motion of the subject) have been eliminated from the output of the photoelectric sensor 26. The processing carried out by the pulse wave reproducing circuit 57 constitutes a modifying process in the invention. Output data of the photoelectric sensor 26 is thus processed through the noise eliminating process by the low-pass and high-pass filters 53 and 54 and the modifying process in which the body motion sensor 51 detects slight body motion of the subject 5 and body motion components are subtracted from the output of the photoelectric sensor 26, whereupon only pure pulse wave components are continuously extracted. Consequently, since error components are eliminated from the photoelectric volume pulse waveform, an accurate photoelectric volume pulse wave can be obtained.

Figure 11:
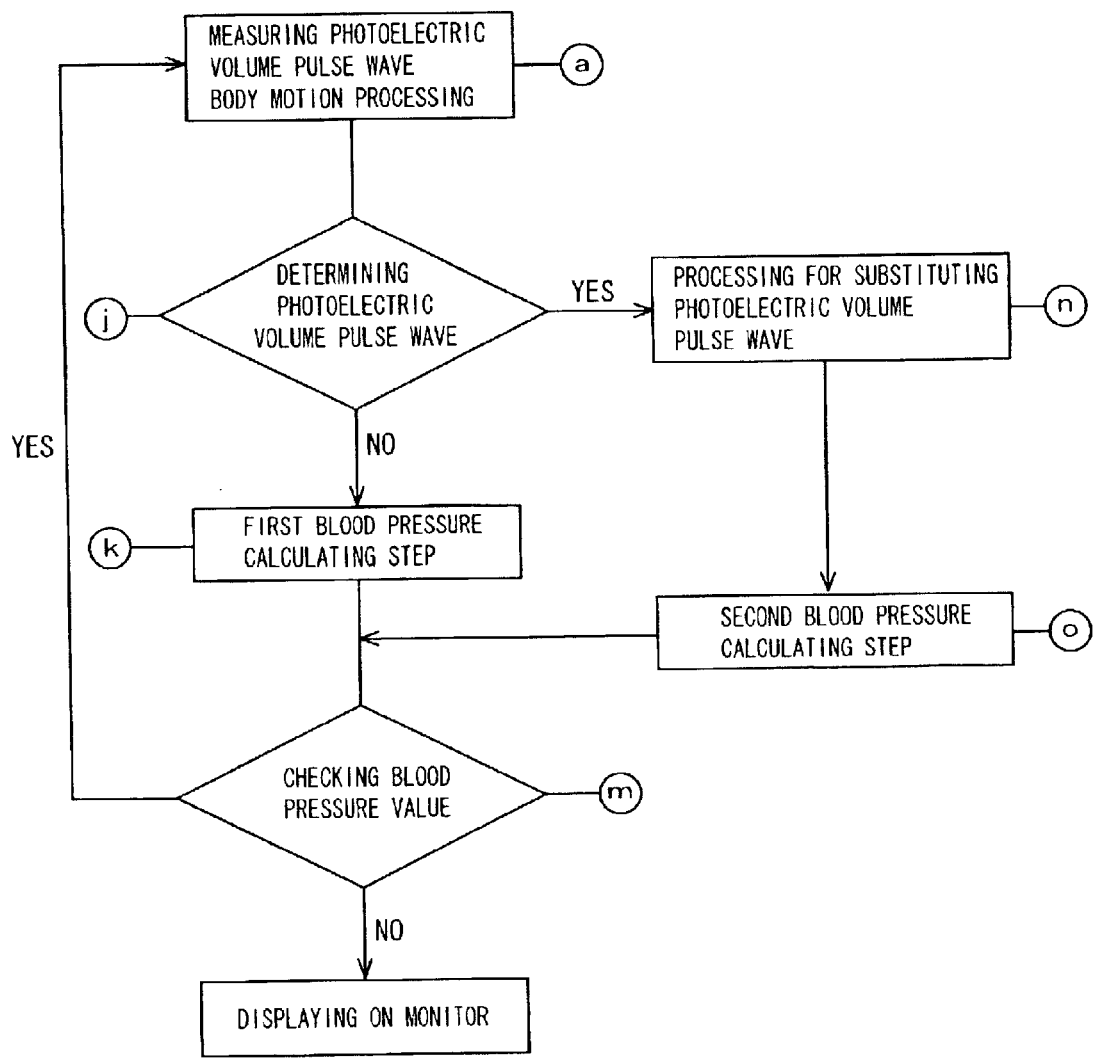
FIG. 11 is a flowchart showing a procedure for calculating a blood pressure value.

Determination of the photoelectric volume pulse wave by the data processing device 10 will now be described with reference to FIG. 11. In the third embodiment, the determination of the photoelectric volume pulse wave depends upon whether a period of the photoelectric volume pulse wave is within a predetermined allowed range (step j). The predetermined allowed range is a normal range of the period of the photoelectric volume pulse wave, for example, a range of 0.75 to 1.5 sec. When a large body motion occurs, in the subject 5 during measurement of a photoelectric volume pulse wave, the waveform of the photoelectric volume pulse wave is disturbed such that the period thereof is Out of the allowed range. When determining that the period of the photoelectric volume pulse wave is within the allowed range, the data processing device 10 advances to a first blood pressure calculating step (step k), whereas the data processing device 10 advances to a step in which the substitution of the photoelectric volume pulse wave is carried out (step n) when determining that the period of the photoelectric volume pulse signal is out of the allowed range.

In the first blood pressure calculation step, a blood pressure variation amount $\Delta P$ and a blood pressure value Pt of the subject in the non-rested state are calculated on the calculated basis of the flow velocity value Vo and blood pressure value Po in the rested state, the peak value of the photoelectric volume pulse wave etc. The data processing device 10 then collates the obtained blood pressure value Pt with the blood pressure reference value, thereby checking it (step m). The blood pressure reference value is a range of blood pressure obtained by a normal measurement (for example, range of 50 to 140 mmHg). When the obtained blood pressure value is within the reference value range, the data processing device 10 determines that the measurement has normally been carried out, displaying the transition of blood pressure Pt. On the other hand, when the obtained blood pressure value is out of the reference value range, the data processing device 10 determines that measurement is erroneous, returning to the pulse wave measuring step (step a) for re-calculation of the blood pressure value Pt.

Figure 12A:
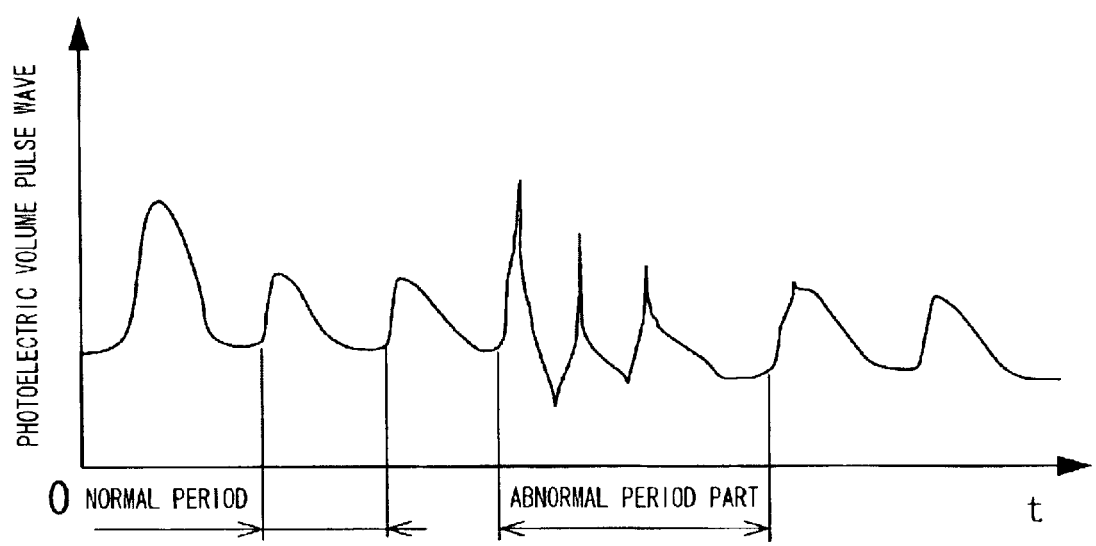
FIGS. 12A and 12B are graphs showing transition of photoelectric volume pulse wave before and after substitution respectively.
Figure 12B:
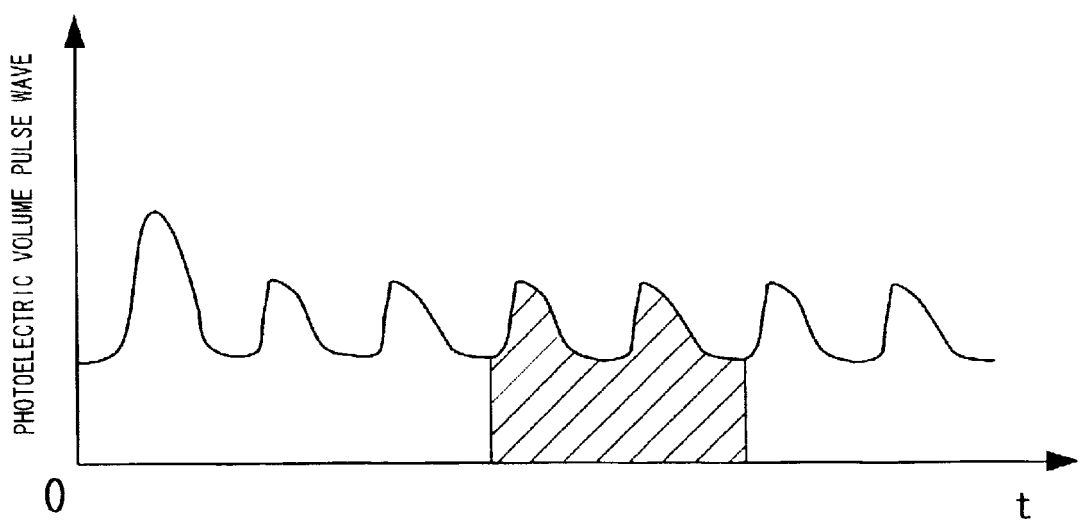

When determining that the period of photoelectric volume pulse wave is out of the allowed range, the data processing device 10 executes a substitution processing for the photoelectric volume pulse wave. In the substitution processing, as shown in FIGS. 12A and 12B, a mean waveform model (a hatched portion in FIG. 12B) which will be described later is substituted for abnormal waveform part of the measured photoelectric volume pulse wave or part of waveform data out of the allowed range. Thereafter, a blood pressure value is calculated in a second blood pressure value calculating step (step o). More specifically, regarding part of the waveform data within the allowed range, a flow velocity value Vo and blood pressure value Po in the subject's rested state are calculated, and a blood pressure variation amount $\Delta P$ is calculated on the basis of a peak value of the photoelectric volume pulse wave etc. A blood pressure value Pt in the subject's non-rested state is lastly calculated. Regarding the part of waveform data out of the allowed range, a blood pressure variation amount $\Delta P$ and a blood pressure value Pt in the subject's non-rested state are calculated on the basis of the substituted peak value of photoelectric volume pulse wave. Thereafter, the data processing device 10 advances to step m to check the blood pressure value.

The mean waveform model is calculated on the basis of waveform data of the subject 5 within the allowed range. More specifically, waveform data of photoelectric volume pulse wave is supplied into the storage area 13 at any time after start of measurement. On the other hand, CPU 12 calculates a mean value on the basis of a peak value and period etc. regarding the waveform data which has been measured until detection of waveform data which is out of the allowed range. CPU 12 then obtains a mean waveform model based on the results of calculation.

As obvious from the foregoing, since the data processing device 10 carries out determination of the photoelectric volume pulse wave, error due to such a large body motion that cannot be detected by the body motion sensor 51 can be eliminated and furthermore, an accurate photoelectric volume pulse wave can be obtained. Accordingly, a reliable diagnosis can be made when data analysis (for example, calculation of a mean blood pressure value) is carried out about a blood pressure value after detection of the blood pressure value.

The photoelectric volume pulse wave is measured at the wrist of the subject 5 (measurement part) in the embodiment. However, an error sometimes occurs in the measurement because a vertical distance between the measurement part and the heart of the subject differs depending upon an angle of the subject's arm. An angular compensation can be made by the CPU 12 when an angle sensor is provided for detecting an angle of the subject's arm as a measure to prevent the foregoing error.

Figure 13:
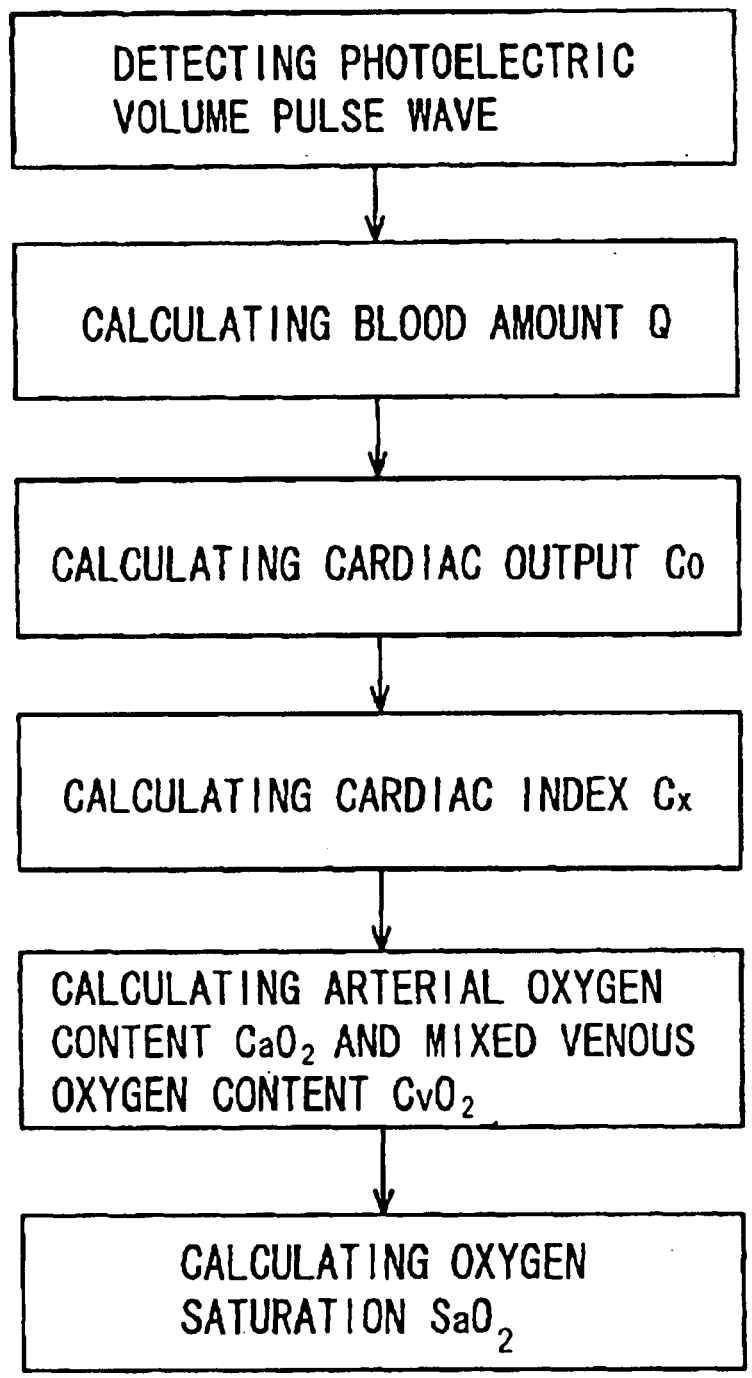
FIG. 13 is a flowchart showing a procedure for calculating an oxygen saturation of arterial blood.
Figure 14:
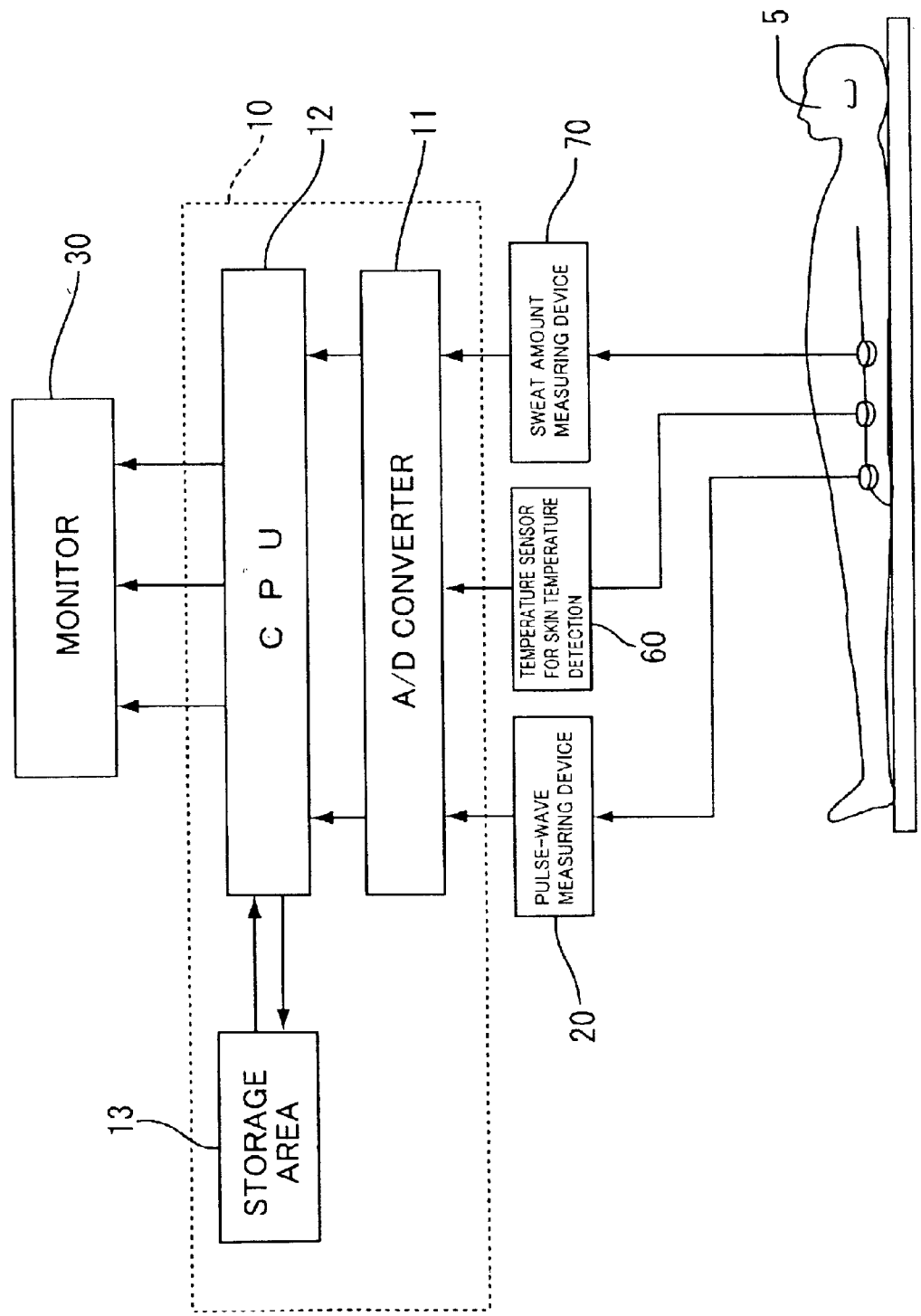
FIG. 14 is a block diagram of the biological data observation apparatus in accordance with a fourth embodiment of the present invention.
Figure 15:
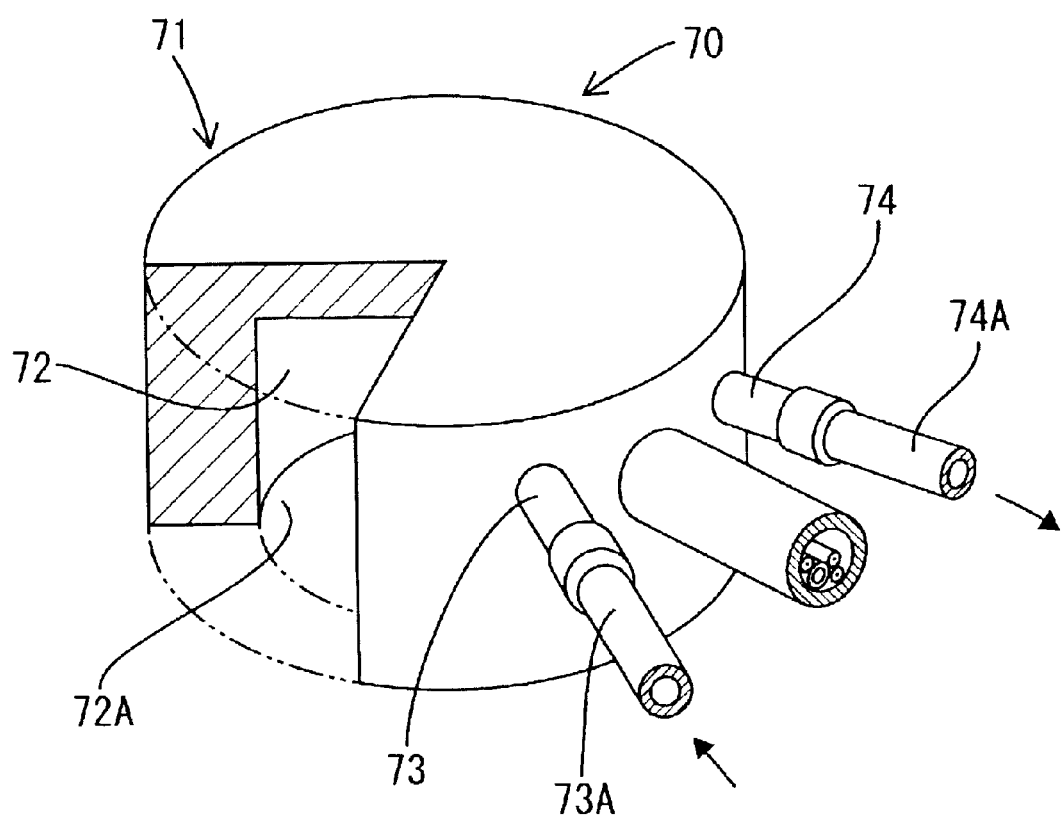
FIG. 15 is a partially broken perspective view of a capsule of a sweat amount measuring device.

The data processing device 10 can calculate an oxygen saturation of arterial blood $SaO_2$ as well as the above-described blood pressure value. A calculating procedure will be described with reference to FIG. 13. The data processing device 10 calculates a blood flow rate Q on the basis of the blood pressure and flow velocity conversion data and photoelectric volume pulse wave and further calculates a pulsation E on the basis of a period of the photoelectric volume pulse wave. The data processing device 10 further calculates a cardiac output Co and a cardiac index Cx from the following equations (8) and (9):

$$Co = E \cdot Q \qquad (8)$$

$$Cx = Co/S \qquad (9)$$

where E is pulsation and S is body surface area (S=3.4 L/min/m² in the embodiment). The data processing device 10 further calculates an arterial oxygen content $CaO_2$ and a mixed venous oxygen content $CvO_2$ from a known algorithm on the basis of the photoelectric volume pulse wave and further calculates an oxygen saturation of arterial blood $SaO_2$ from the following equation (10):

$$SaO_2 = (CaO_2 - CvO_2) \cdot Cx \qquad (10)$$

A fourth embodiment of the invention will be described with reference to FIGS. 14 to 21. Although only the pulse-wave measuring device 20 constitutes the measuring unit and measures mainly a blood pressure in the first embodiment, the measuring unit comprises a sweat amount measuring device 70 serving as a sweat amount measuring section and a temperature sensor 60 for detecting a skin temperature and serving as skin temperature measuring section, in addition to the pulse-wave measuring device 20. A degree of anesthesia (which will hereinafter be referred to as "anesthesia depth"), is calculated on the basis of the results of detection by the afore-mentioned devices. The other arrangement in the fourth embodiment is similar to that in the first embodiment and accordingly, detailed description of the other arrangement will be eliminated. Biological data obtained by each measuring devices will hereinafter be referred to as "primary biological data."

Firstly, the sweat amount measuring device 70 will be described. The sweat amount measuring device 70 has the same operating principle as a sweat amount measuring device disclosed in JP-A-10-262958 filed by the assignee of the present application. More specifically, the sweat amount measuring device 70 includes a capsule 71 having a recess 72. The capsule 71 is attached to the skin surface of the subject with an opening of the recess 72 being closed by the skin surface. The capsule 71 includes a side formed with a supply opening 73 and a discharge opening 74 both communicating with the recess 72. A low-humidity nitrogen gas reserved in a cylinder (not shown) is supplied at a predetermined flow rate into the recess 72 through a rubber tube 73A communicating with the supply opening 73. On the other hand, a humidifier (not shown) is provided in the middle of a rubber tube 74A communicating with the discharge opening 74 for measuring a humidity of air discharged. Furthermore, the capsule 71 includes a thermometer and a heater-cooler (for example, Peltier element) both built therein so that an interior of the recess 72 is maintained at a constant temperature. The sweat amount measuring device 70 has an output line connected via the A/D converter 11 to the CPU 12 so that output of the humidifier and thermometer is supplied into the data processing device 10. The data processing device 10 executes an operation on the basis of the supplied output, obtaining a sweat amount of the subject (sweat amount data).

The temperature sensor 60 for the detection of skin temperature may be of the thermal expansion type, thermocouple type or thermistor type. The temperature sensor 60 is attached to an arm of the subject 5 etc. for measuring purpose, thereby detecting a skin temperature of the subject. The temperature sensor 60 also has an output line connected via the A/D converter to the CPU 12. Output of the temperature sensor 60 is supplied into the data processing device 10, which then executes an operation on the basis of the supplied output to obtain a skin temperature of the subject 5 (skin temperature data).

Furthermore, the data processing device 10 calculates peak value data regarding a peak value and pulsation data on the basis of the photoelectric volume pulse wave obtained from the pulse-wave measuring device 20. The data processing device 20 further calculates a flow velocity value on the basis of flow velocity conversion data and further calculates an oxygen saturation of arterial blood (oxygen saturation data) on the basis of the obtained flow velocity value. The data processing device 10 calculates an anesthesia depth T based on the obtained primary biological data.

Two methods for measurement of anesthesia depth T will be described. In a first method, the data processing device 10 obtains composite data from the primary biological data and calculates an anesthesia depth T based on the obtained composite data. Firstly, peak value data y1 serves as reference data. The other primary biological data (sweat amount data y2, oxygen saturation data y3, skin temperature data y4 and pulsation data y5) are added to the reference data on the basis of an algorithm as shown in the following equation (11) so that composite data A is obtained:

$$A = h1 \cdot y1 + h2 \cdot F(y2) + h3 \cdot G(y3) + h4 \cdot H(y4) + H5 \cdot I(y5) \qquad (11)$$

where y1 is peak value data, y2 is sweat amount data, y3 is oxygen saturation data, y4 is skin temperature data, y5 is pulsation data, h1 to h5 are constants, and F to I are functions. The peak value data is selected as the reference data as described above. The reason for this selection is that the peak value data shows a best correlation with the degree of anesthesia when the anesthesia depth is represented as numeric.

Composite data is obtained as will be described below. Firstly, the sweat amount data y2 and peak value data are formed into composite data. More specifically, composite data A2 of the sweat amount data y2 and peak value data y1 is obtained from equation (11):

$$A2 = h1 \cdot y1 + h2 \cdot F(y2)$$

Figure 16A:
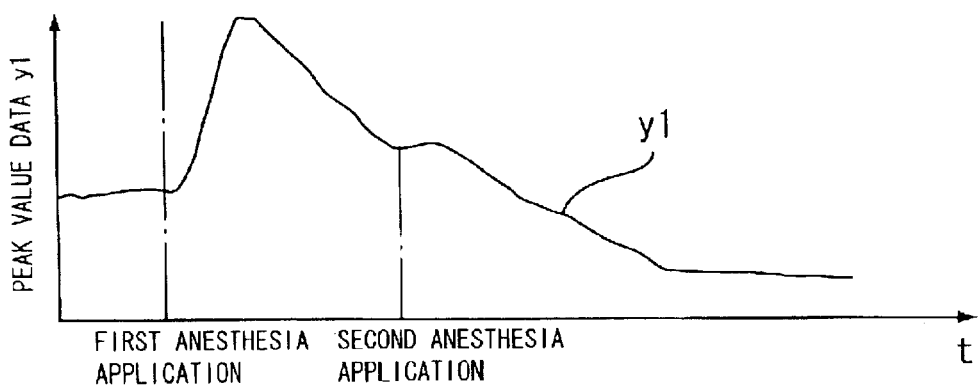
FIG. 16A is a graph showing transition of peak value data of a photoelectric volume pulse wave.
Figure 16B:
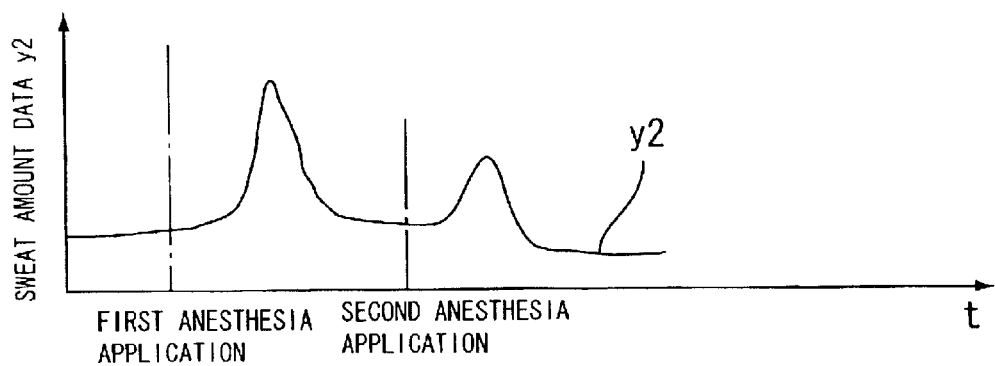
FIG. 16B is a graph showing transition of sweat amount data.
Figure 16C:
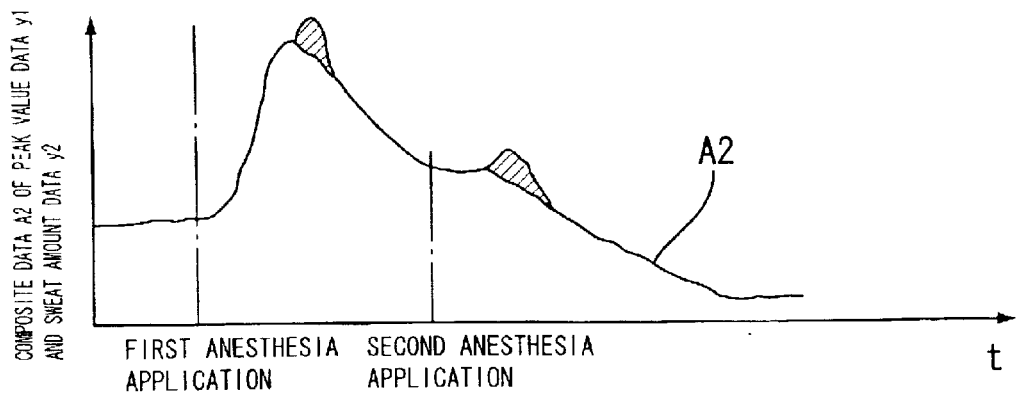
FIG. 16C is a graph showing transition of composite data A2.
Figure 17:
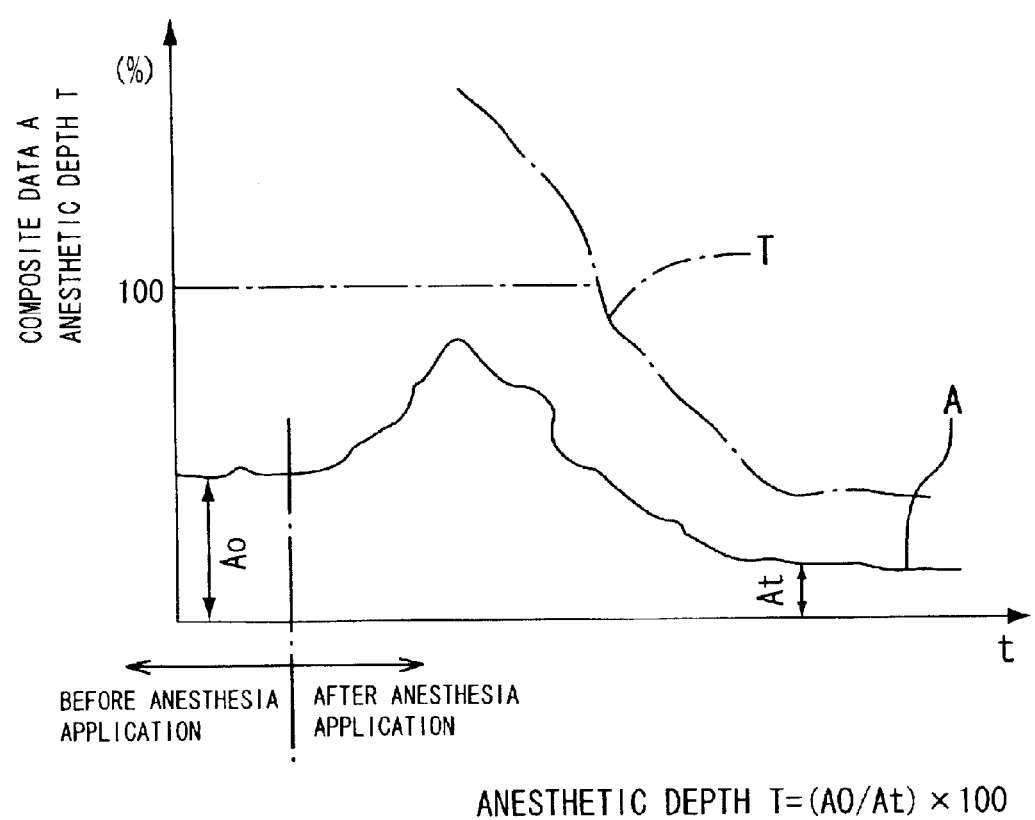
FIG. 17 is a graph showing transition of anesthesia depth.
Figure 18A:
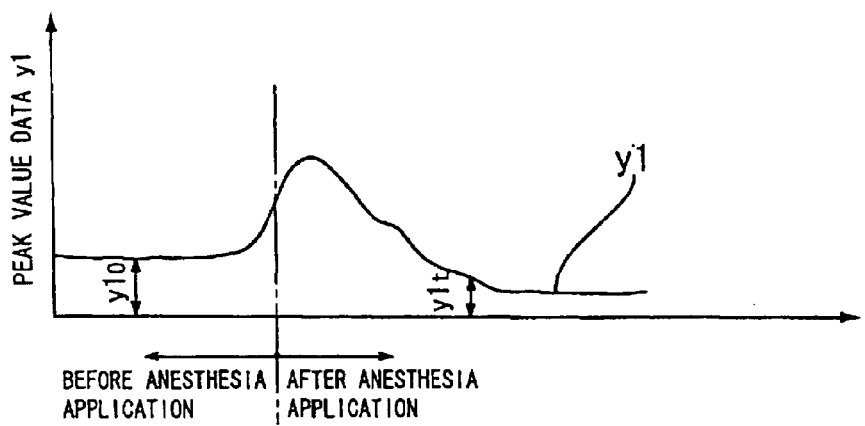
FIGS. 18A and 18B are graphs showing transition of primary biological data.
Figure 18B:
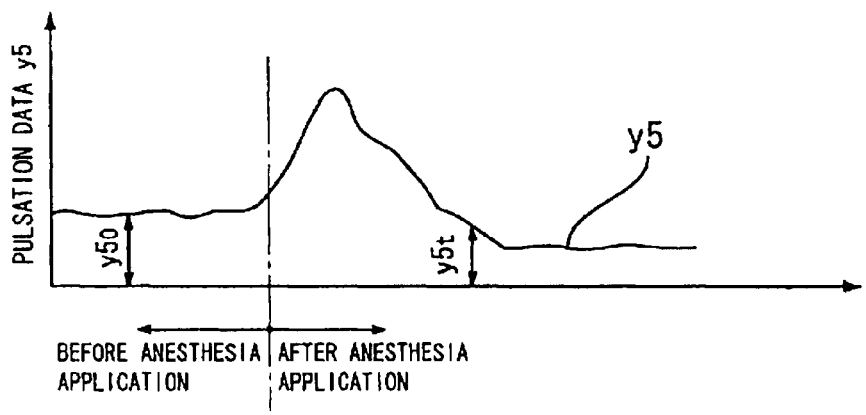
Figure 19A:
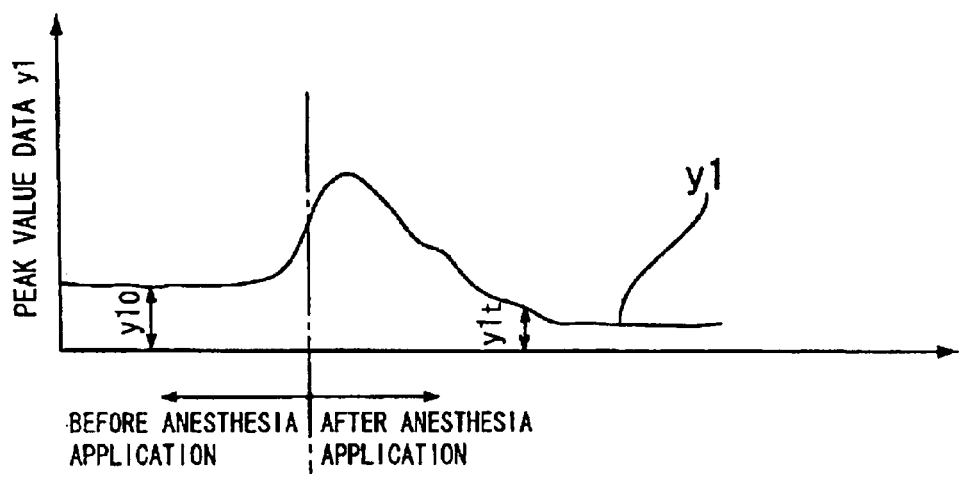
FIGS. 19A and 19B are graphs showing transition of other biological data.
Figure 19B:
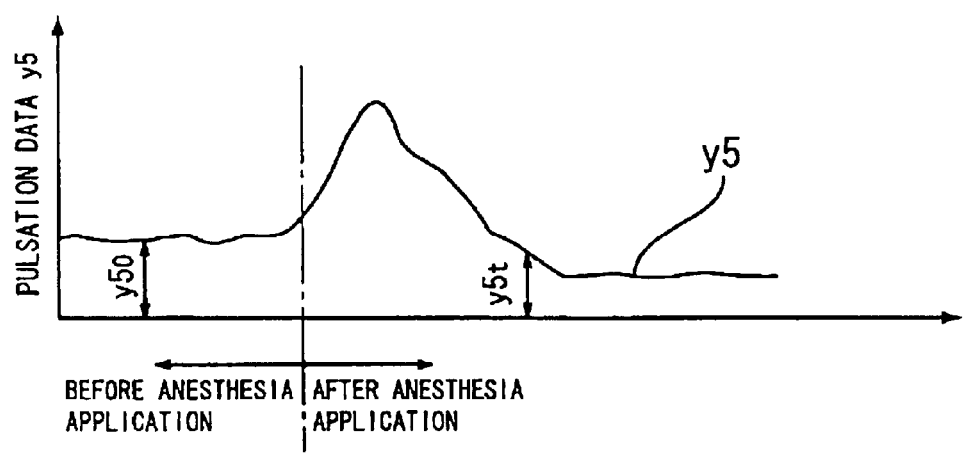

Since $F(y2) = 1 - \exp(-h6 \cdot y2)$ $$A2 = h1 \cdot y1 + h2 \cdot (1 - \exp(-h6 \cdot y2))$$

where h6 is a constant. In the obtained composite data A2 of the peak value data y1 and the sweat amount data y2, transition of the peak value data serves as a base, to which transition of the sweat amount data y2 is added, as shown in FIG. 16C. More specifically, small transition in the sweat amount data y2 have less effect on transition in the peak value data y1, and only a large transition in the sweat amount data y2 appears on the peak value data y1 with a reduced scale (hatched portion in FIG. 16C).

Each of the oxygen saturation data y3, skin temperature data y4 and pulsation data y5 is synthesized into the composite data A2 as in the same manner as described above, whereupon the composite data is calculated. See FIG. 17. The anesthetic depth T is calculated on the basis of the composite data obtained as described above:

$$T = At/Ao \cdot 100 \qquad (12)$$

where Ao is a reference value of composite data A (the value before application of anesthesia), and At is a value At of the composite data A after application of anesthesia. The anesthetic depth T is thus obtained as an absolute value on the basis of a ratio of the reference value Ao of the composite data A to the value At of composite data after application of anesthesia. Furthermore, transition of the calculated anesthesia depth is displayed on the monitor 30 with the composite data A.

In the fourth embodiment, a plurality of primary biological data closely related with a degree of anesthesia are put together into a signal data for the purpose of measuring the anesthesia depth. Accordingly, since a plurality of primary biological data are compensated by one another, a more accurate anesthetic depth T can be obtained as compared with the case where the anesthetic depth is calculated on the basis of a single primary biological data.

The calculated composite data A is stored in the storage area 13. Even if measurement of the primary biological data about the subject 5 starts after application of anesthesia, the anesthetic depth T can be calculated. More specifically, the data processing device 10 collates a change pattern (transition from start of measurement to stabilization of composite data) of composite data B calculated on the basis of the primary biological data with change patterns of accumulated previous composite data, thereby extracting similar composite data R. The reference value Ro of the extracted composite data R is substituted for the composite data B. The anesthetic depth of the subject 5 is calculated on the basis of the substituted reference value Ro and a value Bt of the composite data B:

$$T = Bt/Ro \cdot 100$$

In the embodiment, a reference value Ao used for calculation of the anesthetic depth is the one obtained after application of anesthesia. However, any value composing composite data A may be used. For example, a peak value obtained after application of anesthesia may be used.

A second calculating method will now be described with reference to FIGS. 18A to 20. In this method, an anesthetic depth is calculated for each primary biological data. Thereafter, the anesthetic depth values calculated on the basis of the respective primary biological data are added together, so that a synthetic anesthetic depth is obtained. Calculation exemplified here is based on the peak value data y1, sweat amount data y2, oxygen saturation data y3 and pulsation data y5. However, the calculation may be based on only the peak value data y1, sweat amount data y2 and pulsation data y5.

Firstly, when the peak value data y1, sweat amount data y2, oxygen saturation data y3 and pulsation data y5 are supplied into the data processing device 10, the CPU 12 calculates a mean value of each primary biological data before application of anesthesia, that is, a mean value y1o of peak value data y1, mean value y2o of sweat amount data y2, mean value y3o of oxygen saturation data y3 and mean value y5o of pulsation data y5. Thereafter, the CPU 12 calculates a pulse-wave anesthetic depth T1, sweat-amount anesthetic depth T2 and oxygen-saturation anesthetic depth T3 on the basis of the respective primary biological data according to the respective equations:

$$T1 = y1t \cdot y5t - k1 \cdot y5o)/(k2 \cdot y1o \cdot y5o) \tag{13}$$

$$T2 = (y2t - k3 \cdot y2o)/(k4 \cdot y2o) \tag{14}$$

$$T3 = (y3t - k5 \cdot y3o)/(k6 \cdot y3o) \tag{13}$$

where k1 to k6 are constants, y1o is a mean value of peak value data y1 before application of anesthesia, y1t is a value of peak value data y1 at any time, y5o is a mean value of pulsation data y5 before application of anesthesia, y5t is a value of pulsation data y5 at any time, y2o is a mean value of sweat amount data y2 before application of anesthesia, y2t is a value of sweat amount data y2 at any time, y3o is a mean value of oxygen saturation data y3 before application of anesthesia, and y3t is a value of oxygen saturation data y3 at any time.

Successively, the pulse-wave anesthetic depth T1, sweat-amount anesthetic depth T2 and oxygen-saturation anesthetic depth T3 are added together, whereupon an anesthetic depth T (T=T1+T2+T3) can be calculated. In this case, too, a plurality of primary biological data related with an anesthetic depth are put together into a single data in the same manner as described above. Accordingly, since a plurality of primary biological data are compensated with one another, a more accurate anesthetic depth T can be obtained as compared with the case where the anesthetic depth is calculated on the basis of a single primary biological data.

Figure 20:
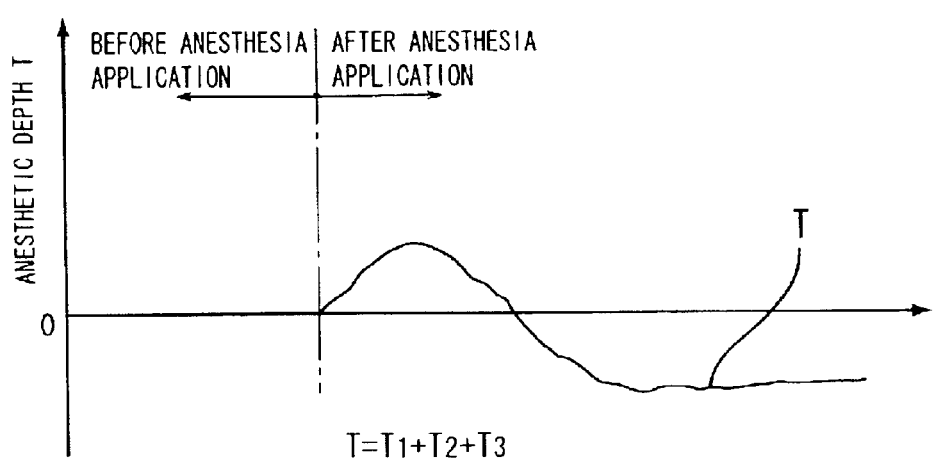
FIG. 20 is a graph showing the anesthesia depth.

Transition of the obtained anesthetic depth T is displayed on the monitor 30 (see FIG. 20). While confirming transition of anesthetic depth T on the monitor 30, the doctor adjusts an amount of anesthesia applied to the subject 5. The doctor starts operation when understanding that the anesthetic depth T is stable at a suitable value. On the other hand, in a case where the subject 5 has an abnormal symptom, the doctor learns the abnormal symptom when viewing transition of anesthetic depth on the monitor 30. In this case, when alarming means is provided in the data processing device 10, the doctor can be informed of the abnormal symptom of the subject 5 without depending upon the contents displayed on the monitor 30.

Figure 21:
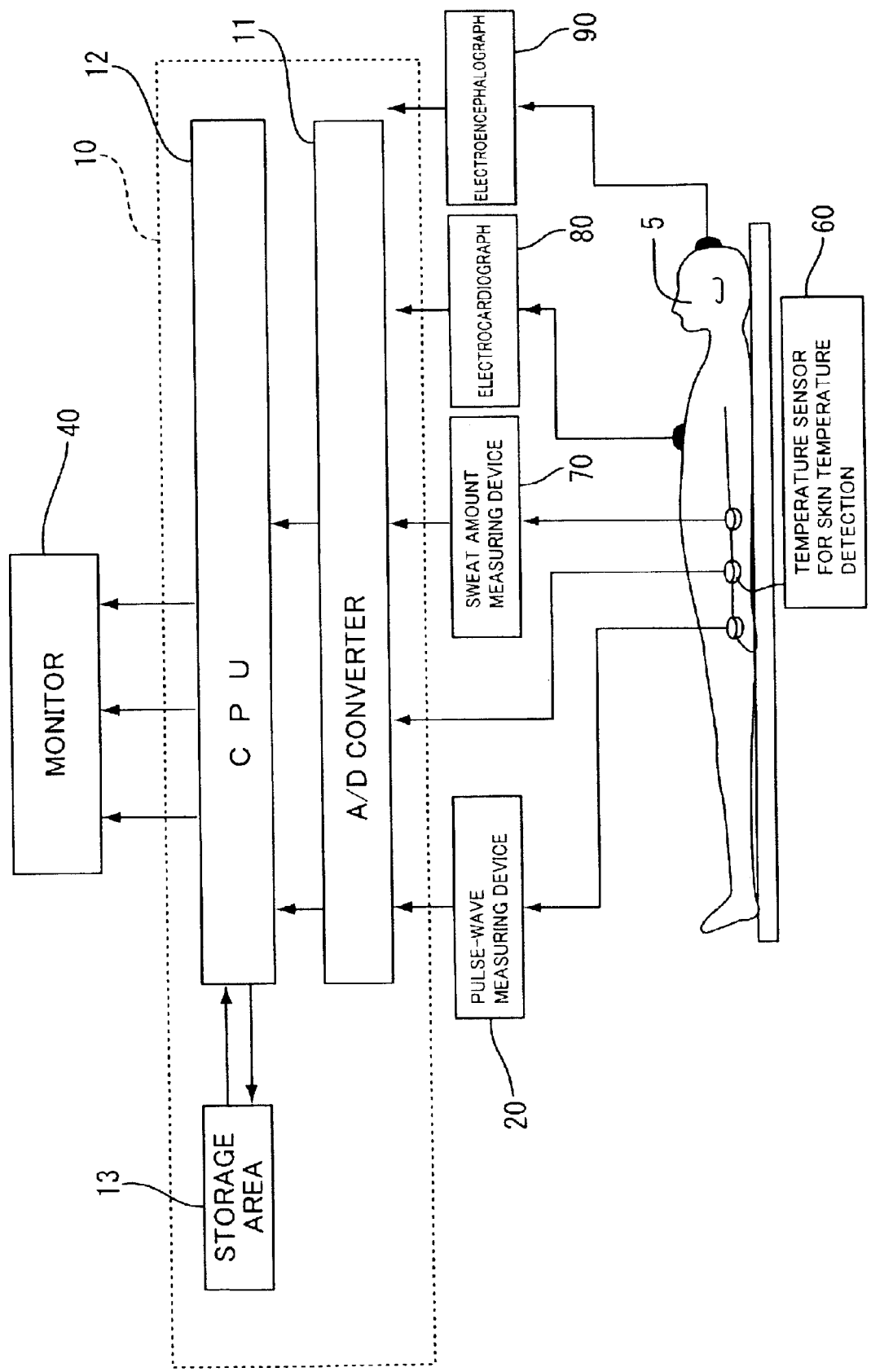
FIG. 21 is a block diagram of the biological data observation apparatus to which an electrocardiograph and an electroencephalograph are added.

An electrocardiograph 80 serving as a heartbeat measuring section and an electroencephalograph 90 serving as a brain wave measuring section may be provided in addition to the above-described measuring unit as shown in FIG. 21. The electrocardiograph 80 includes electrodes applied to the body surface of the subject 5 for detecting a feeble electric signal generated when the heart beats. The electric signal is amplified by an amplifier to be delivered as heart-beat data y6.

The electroencephalograph 90 has the same operating principle as the electrocardiograph 80 and includes electrodes applied to the head of the subject 5 for detecting a feeble electric signal generated in the brain as the result of working of the brain. The signal is amplified by the amplifier to be delivered as brain wave data y7.

The data processing device 10 calculates the anesthetic depth T based on the seven primary biological data, that is, the peak value data y1, sweat amount data y2, oxygen saturation data y3, skin temperature data y4, pulsation data y5, heart-beat data y6 and brain wave data y7. Further accurate anesthetic depth T can be calculated since the heart beat and brain wave are parameters closely related with the anesthetic depth T.

Figure 22A:
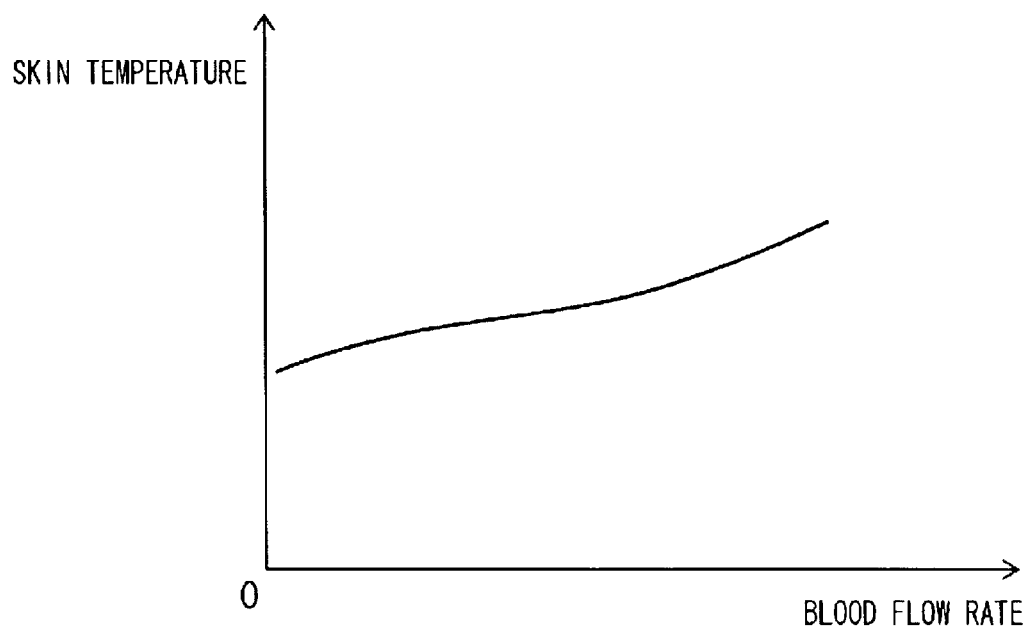
FIGS. 22A and 22B are graphs showing correlations between skin temperature and sweat amount, and blood flow amount respectively.
Figure 22B:
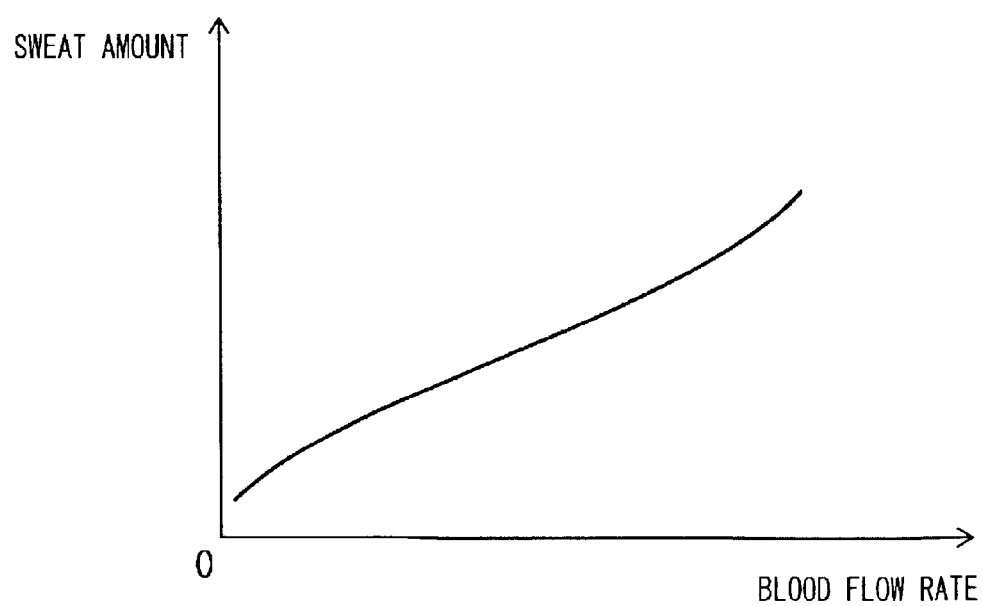

A fifth embodiment of the invention will be described with reference to FIGS. 22A and 22B. Although the anesthetic depth T of the subject 5 is calculated in the fourth embodiment, a total calorie of the subject 5 is calculated.

In the fifth embodiment, the biological data observation apparatus includes a temperature sensor 60 serving as the measuring unit and detecting a skin temperature. On the other hand, the storage area 13 stores body surface area conversion data which will be described below. The body surface area conversion data contains a correlation between a person's figure and body surface area. For example, a person's body surface area is calculated when data of height, weight, age and sex of the person is entered. Accordingly, when a skin temperature of the subject 5 is measured by the temperature sensor 60 and a mean value of the measured skin temperatures per predetermined time is calculated by the CPU, a total calorie of the subject 5 can be calculated on the basis of the mean skin temperature value and the body surface area.

Furthermore, when the pulse-wave measuring device 20 and the temperature sensor 60 are used together, the skin temperature of the subject 5 can also be calculated on the basis of the photoelectric volume pulse wave. More specifically, the inventors have found that a skin temperature has a relation with a blood flow rate. Accordingly, a photoelectric volume pulse wave is measured by the pulse wave measuring device 20 so that a peak value of the photoelectric volume pulse wave is obtained. A flow velocity value is calculated on the basis of flow velocity conversion data, and a blood flow rate is calculated. Skin temperature and blood flow conversion data is calculated on the obtained blood flow rate and skin temperature (see FIGS. 22A and 22B.). The skin temperature and the blood flow rate are correlated with each other in the calculated conversion data. The skin temperature and blood flow conversion data is written into the storage area 13 for every subject 5. As a result, after the conversion data has been written, the skin temperature of the subject 5 can be calculated on the basis of the skin temperature and blood flow conversion data written in the storage area 13 when the photoelectric volume pulse wave is measured by the pulse wave measuring device 20 without direct measurement by the temperature sensor 60. When the skin temperature and blood flow conversion data is written into the storage area 13, it is desirable that the data should be written together with data of environment (humidity, temperature, etc.) at the time of measurement. Consequently, factors which result in errors are eliminated and accordingly, accurate data can be obtained.

Furthermore, the inventors have found that a sweat amount also has a relation with a blood flow rate. Accordingly, a sweat amount of the subject 5 can be calculated without direct measurement of sweat amount when both primary biological data of sweat amount and blood flow rate are obtained and sweat amount and blood flow rate conversion data is calculated on the basis of the primary biological data.

In modified forms, an animal may be used although the artificial measurement human body model 40 is used in the first embodiment. Furthermore, the blood flow rate per heart-beat is measured by the photo electric sensor 26 in the first embodiment. However, the heart-beat maybe measured using laser beams, other light sources or an ultrasonic sensor or pressure sensor.

In the first embodiment, the blood flow rate of the subject 5 is measured by the photoelectric sensor 26 of the fixed type in order that the arteriosclerosis may be detected. However, a photoelectric sensor of the scanner type may be used, instead.

The photoelectric sensor 26 of the single waveform type is used in each of the first to fifth embodiments. However, the photoelectric sensor may be of multiple wavelength type (dual or triple wavelength).

The foregoing description and drawings are merely illustrative of the principles of the present invention and are not to be construed in a limiting sense. Various changes and modifications will become apparent to those of ordinary skill in the art. All such changes and modifications are seen to fall within the scope of the invention as defined by the appended claims.

What is claimed is:

1. A biological data observation apparatus comprising:

a measuring unit including at least a photoelectric sensor including a light emitting element for emitting light with a predetermined wavelength onto a blood vessel of a subject and a light detecting element for detecting, as a photoelectric capacity pulse wave, a change in an amount of transmitted or reflected light resulting from the light emitted from said light emitting element;

a storage area in which blood pressure conversion data, correlating a pulse wave area and a blood pressure value in order that a pulse wave area may be converted to a blood pressure value as an absolute value, is stored, the pulse wave area being obtained by integrating a waveform of the photoelectric volume pulse wave per heartbeat;

an operational unit calculating the pulse wave area on the basis of the photoelectric volume pulse wave obtained from the subject and further calculating a blood pressure value of the subject on the basis of the calculated pulse wave area and the blood pressure conversion data; and a display unit displaying a result of calculation performed by said operational unit, wherein the blood pressure conversion data is calculated on the basis of a measuring artificial human body model including a liquid feeding unit and a pressure measuring section, wherein the liquid feeding unit pressure-feeds blood or an equivalent thereof per heartbeat time obtained while a sampling object having a predetermined form is in a rested state, wherein the liquid feeding unit has a pressure adjustable pressure feed, and a transfer tube through which the blood or equivalent thereof is transferred, wherein the transfer tube has an inner diameter substantially equal to an inner diameter of a blood vessel of the sampling object near which blood pressure is measured by a second photoelectric sensor while the sampling object is in the rested state, wherein the pressure measuring section measures pressure of the blood or equivalent thereof in the transfer tube, wherein the second photoelectric sensor irradiates light with a predetermined wavelength onto the transfer tube for detecting, as a photoelectric volume pulse wave of the transfer tube, a change in an amount of transmitted or reflected light resulting from the irradiated light, wherein the pressure applied to the blood or equivalent thereof during the pressure feed is varied into various values, wherein the photoelectric volume pulse wave of the transfer tube and the pressure applied to the blood or equivalent thereof during the pressure feed are measured by the second photoelectric sensor and the pressure measuring section respectively so that the pulse wave area of the photoelectric volume pulse wave of the transfer tube per heartbeat time and the pressure value of the blood or equivalent thereof both obtained by the second photoelectric sensor and the pressure measuring section respectively are correlated with each other, wherein said measuring unit further includes another photoelectric sensor including a an other single light emitting element and a plurality of light detecting elements which are disposed along the blood vessel of the subject so as to be spaced each one from the other, wherein said operational unit calculates a pulse wave area So on the basis of a photoelectric volume pulse wave obtained from the subject who is temporarily under the measuring reference state prior to measurement, further calculates a blood pressure value Po on the basis of the calculated pulse wave area So and the blood pressure conversion data, and still further calculates a flow velocity Vo in the measuring reference state on the basis of a phase difference between the photoelectric volume pulse waves obtained from said plurality of light detecting elements and distances between said plurality of light detecting elements, and wherein said operational unit calculates a flow velocity Vt in any period on the basis of a phase difference between the photoelectric volume pulse waves obtained from said plurality of light detecting elements and distances between said plurality of light detecting elements, and substitutes the flow velocity values Vo and Vt and the blood density $\rho$ for those in the equation $\Delta P = Pt - Po = \rho/2(Vo^2 - Vt^2)$ thereby to calculate a blood pressure variation amount $\Delta P$ representative of variations in the blood pressure in any period, and calculates the blood pressure value Pt in any period from the calculated blood pressure variation amount $\Delta P$ and the blood pressure value Po at the measurement reference time.

2. A biological data observation apparatus comprising:

a measuring unit including at least a photoelectric sensor including a light emitting element for emitting light with a predetermined wavelength onto a blood vessel of a subject and a light detecting element for detecting, as a photoelectric capacity pulse wave, a change in an amount of transmitted or reflected light resulting from the light emitted from said light emitting element;

a storage area in which blood pressure conversion data, correlating a pulse wave area and a blood pressure value in order that a pulse wave area may be converted to a blood pressure value as an absolute value, is stored, the pulse wave area being obtained by integrating a waveform of the photoelectric volume pulse wave per heartbeat;

an operational unit calculating the pulse wave area on the basis of the photoelectric volume pulse wave obtained from the subject and further calculating a blood pressure value of the subject on the basis of the calculated pulse wave area and the blood pressure conversion data; and a display unit displaying a result of calculation performed by said operational unit, wherein the blood pressure conversion data is calculated on the basis of a measuring artificial human body model including a liquid feeding unit and a pressure measuring section, wherein the liquid feeding unit pressure-feeds blood or an equivalent thereof per heartbeat time obtained while a sampling object having a predetermined form is in a rested state, wherein the liquid feeding unit has a pressure adjustable pressure feed, and a transfer tube through which the blood or equivalent thereof is transferred, wherein the transfer tube has an inner diameter substantially equal to an inner diameter of a blood vessel of the sampling object near which blood pressure is measured by a second photoelectric sensor while the sampling object is in the rested state, wherein the pressure measuring section measures pressure of the blood or equivalent thereof in the transfer tube, wherein the second photoelectric sensor irradiates light with a predetermined wavelength onto the transfer tube for detecting, as a photoelectric volume pulse wave of the transfer tube, a change in an amount of transmitted or reflected light resulting from the irradiated light, wherein the pressure applied to the blood or equivalent thereof during the pressure feed is varied into various values, wherein the photoelectric volume pulse wave of the transfer tube and the pressure applied to the blood or equivalent thereof during the pressure feed are measured by the second photoelectric sensor and the pressure measuring section respectively so that the pulse wave area of the photoelectric volume pulse wave of the transfer tube per heartbeat time and the pressure value of the blood or equivalent thereof both obtained by the second photoelectric sensor and the pressure measuring section respectively are correlated with each other, wherein the measuring model has a flow rate measuring section measuring a flow rate of the blood or equivalent thereof per heartbeat time, wherein said storage area stores flow velocity conversion data, the data including a flow velocity value obtained by dividing a flow rate measured by the flow rate measuring section by a sectional area of the transfer tube, and the pulse wave area of the photoelectric volume pulse wave measured relative to the transfer tube, the flow velocity and the pulse wave area being correlated with each other, wherein said operational unit calculates a pulse wave area So on the basis of a photoelectric volume pulse wave obtained from the subject while the subject is in a reference state prior to start of measurement, wherein said operational unit further calculates a reference pressure value Po and a reference flow velocity value Vo on the basis of the obtained pulse wave area So, blood pressure conversion data, and flow velocity conversion data, wherein said operational unit further calculates, from the measuring model and an algorithm, a blood pressure variation amount $\Delta P$ indicative of a variation in a blood pressure in a predetermined time after calculation of the reference pressure value Po and the reference flow velocity value Vo on the basis of a change rate in a peak value of the photoelectric volume pulse wave and the reference flow velocity value Vo at the reference time, the algorithm being determined so that a flow velocity Vt at any time is calculated by substituting the flow velocity value Vo, a peak value Do of the photoelectric volume pulse wave, a peak value Dt of the photoelectric volume pulse wave at any time, and a constant k are substituted into an equation (a) and, the blood pressure variation amount $\Delta P$ is obtained by substituting the reference flow velocity value Vo at the reference time, a flow velocity Vt at any time, and a blood density $\rho$ into an equation (b), wherein equation (a) is $Vt(Do/kTh)^2 \cdot Vo$, and wherein equation (b) is $\Delta P = Pt - Po = \rho/2(Vo^2 - Vt^2)$, where Pt is a blood pressure value in any period.

3. A biological data observation apparatus according to claim 2 wherein:
said measuring unit includes at least a blood pressure measuring section measuring a blood pressure value of a subject;
said storage area stores blood pressure and blood flow conversion data in which the blood pressure and an amount of blood flow measured from the measuring artificial human body model are correlated with each other;
said operational section receives results of measurement measured by said measuring section, further calculates said blood pressure value of the subject in a predetermined time obtained on the basis of said algorithm by operational processing, and further calculates a blood flow amount of the subject from the calculated blood pressure value of the subject and the blood pressure and blood flow conversion data; and
said display unit displays a result of the further calculation carried out by said operational section.

4. A biological data observation apparatus according to claim 2, wherein the liquid feeding unit further includes a plurality of transfer tubes having different diameters according to differences in individual subjects,
wherein the blood pressure conversion data and the flow velocity conversion data is calculated for each transfer tube,
wherein said storage area stores a plurality of data tables so that the blood pressure conversion data and the flow velocity conversion data with respect to the plurality of transfer tubes with the different diameters are written into the data tables respectively,
wherein said measuring unit includes a blood vessel diameter measuring section measuring a diameter of a blood vessel of the subject in a rested state in addition to the photoelectric sensor, and
wherein based on results of measurement by said blood vessel diameter measuring section, said operational unit selects the data table storing the blood pressure conversion data and the flow velocity conversion data with respect to a transfer tube having a diameter approximate to the measured diameter of blood vessel of the subject.

5. A biological data observation apparatus according to claim 2, wherein said operational unit calculates a cardiac output and arterial oxygen saturation on the basis of the photoelectric volume pulse wave obtained by said photoelectric sensor and blood pressure conversion data.

6. A biological data observation apparatus according to claim 2, wherein said measuring unit further includes a sweat amount measuring section measuring an amount of sweat given forth by the subject and a skin temperature measuring section measuring a temperature of a skin of the subject,
wherein said operational unit calculates a pulse wave area on the basis of the supplied photoelectric volume pulse wave of the subject when the photoelectric volume pulse wave of the subject is supplied thereto, further calculates an amount of blood flowing in the subject on the basis of the calculated pulse wave area and the flow velocity conversion data and further calculates sweat amount conversion data correlating the amount of blood flowing and the sweat amount with each other from the calculated amount of blood flowing and the sweat amount measured by said sweat amount measuring section and skin temperature conversion data correlating the amount of blood flowing and the skin temperature with each other on the basis of the calculated amount of blood flowing and the skin temperature measured by said sweat amount measuring section,
wherein the sweat amount conversion and skin temperature conversion data are calculated for a plurality of subjects, and
wherein said operational unit calculates mean values of the sweat amount and skin temperature of each of said plurality of subjects on the basis of the sweat amount and skin temperature conversion data and the amount of blood of the subject without using the sweat amount and skin temperature measuring sections after the sweat amount and skin temperature data have been written into the storage area.

7. A biological data observation apparatus according to claim 6, wherein said storage area stores body surface area conversion data which correlates personal form data including data of personal stature, weight, age, sex and data of body surface area with each other so that a body surface area of the subject is calculated,
wherein when at least one piece of personal form data regarding the subject has been supplied to said operational unit, said operational unit calculates a body surface area of the subject on the basis of the supplied personal form data and the body surface area conversion data, and
wherein said operational unit further calculates calorie consumption required of the subject on the basis of the calculated body surface area or the skin temperature and a mean value thereof.

8. A biological data observation apparatus according to claim 2, wherein the storage area includes a waveform data storage section storing waveform data of the supplied photoelectric volume pulse wave, wherein the operational unit sets an allowed range the waveform data normally takes, based on the waveform data accumulated in the waveform data storage section,
wherein the operational unit determines whether new waveform data is within the allowed range upon supply of the waveform data thereto, and
wherein when part of the waveform data is out of the allowed range, said operational unit carries out a substituting process in which other waveform data is substituted for the part of the waveform data, the other waveform data being measured until the waveform data out of the allowed range has been detected from start of measurement and determined to be within the allowed range.

9. A biological data observation apparatus according to claim 8, wherein said operational unit calculates the allowed range on the basis of a period of past waveform data written onto the waveform data storage section.

10. A biological data observation apparatus according to claim 9, wherein in the substituting process, said operational unit calculates a mean waveform model on the basis of the periods and peak values of the waveform data measured until the waveform data out of the allowed range has been detected from start of measurement and determined to be within the allowed range.

11. A biological data observation apparatus according to claim 10, wherein said measuring unit includes a body motion sensor irradiating light having a wavelength shorter than a wavelength of the light irradiated by said photoelectric sensor in order to continuously detect an amount of light reflected on the skin surface of the subject, and wherein said operational unit carries out a modifying process in which an output waveform of said body motion sensor is subtracted from an output waveform of said photoelectric sensor in order that a measurement error due to body motion of the subject may be eliminated.

12. A biological data observation apparatus according to claim 2, wherein in addition to said photoelectric sensor, said measuring unit further includes at least any one of:
- a sweat amount measuring section measuring an amount of sweat given forth by the subject;
- a skin temperature measuring section measuring a temperature of a skin of the subject;
- an arterial oxygen saturation measuring section measuring an arterial oxygen saturation of the subject;
- a heartbeat measuring section measuring a heartbeat of the subject; and
- a brain wave measuring section measuring a brain wave of the subject,
- wherein said operational unit calculates an anesthetic depth of the subject on the basis of primary biological data measured by said photoelectric sensor and said at least any one of said sweat amount measuring section, said skin temperature measuring section, said arterial oxygen saturation measuring section, said heartbeat measuring section or said brain wave measuring section.

13. A biological data observation apparatus according to claim 12, wherein said storage area stores data of an algorithm synthesizing different pieces of primary biological data so that a temporal transition is obtained,
- wherein said operational unit synthesizes a plurality of pieces of biological primary data obtained by said measuring unit, on the basis of the algorithm, thereby calculating composite data A, and
- wherein said operational unit further selects, as a reference value Ro, a value at a time approximately before or immediately after application of anesthesia from the calculated composite data A and compares a value At of the composite data A at a time after selection of the reference value Ao, thereby calculating an anesthetic depth.

14. A biological data observation apparatus according to claim 12, wherein said measuring unit includes said photoelectric sensor and said sweat amount measuring section,
- wherein said operational unit incorporates peak value data y1 of the photoelectric volume pulse wave obtained from said photoelectric sensor, heartbeat data y5 and sweat amount data y2 obtained from said sweat amount measuring section thereby to calculate a mean value y1$o$ of the peak value data in a predetermined period before application of anesthesia, a mean value y5$o$ of the heartbeat data y5 in the predetermined period and a mean value y2$o$ of the sweat amount data y2 in the predetermined period,
- wherein said operational unit further obtains a pulse-wave anesthesia depth T1 and a sweat amount anesthesia depth T2 from an equation (13) and an equation (14), respectively, on the basis of the mean values y1$o$, y5$o$ and y2$o$ and a value y1$t$ of the peak value data y1 in a predetermined period after application of anesthesia, a value y5$t$ of the heartbeat data y5 in the predetermined period and a value y2$t$ of the sweat amount data y2, and further calculates an anesthetic depth T (T=T1+T2) on the basis of the obtained pulse-wave anesthetic depth T1 and sweat amount anesthetic depth T2,
- wherein equation (13) is T1=(y1$t$·y5$t$−k1·y1$o$·y5$o$)/(k2·y1$o$·y5$o$),
- wherein equation (14) is T2=(y2$t$−k3·y2$o$)/(k4·y2$o$), and
- wherein k1, k2 and k3 are constants.

* * * * *